(12) United States Patent
Dresios et al.

(10) Patent No.: US 11,639,514 B2
(45) Date of Patent: May 2, 2023

(54) PORTABLE FLUIDIC PLATFORM FOR RAPID CELL-FREE PRODUCTION OF PROTEIN BIOLOGICS

(71) Applicant: Leidos, Inc., Reston, VA (US)

(72) Inventors: John Dresios, Carlsbad, CA (US); Richard Holmes Griffey, Vista, CA (US); Challise J. Sullivan, San Diego, CA (US); Erik D. Pendleton, San Diego, CA (US); Henri M. Sasmor, Oceanside, CA (US); William L. Hicks, San Diego, CA (US); Eric M. Amendt, San Diego, CA (US)

(73) Assignee: Leidos, Inc., Reston, VA (US)

( * ) Notice: Subject to any disclaimer, the term of this patent is extended or adjusted under 35 U.S.C. 154(b) by 513 days.

(21) Appl. No.: 16/846,025

(22) Filed: Apr. 10, 2020

(65) Prior Publication Data
US 2020/0277643 A1 Sep. 3, 2020

Related U.S. Application Data

(62) Division of application No. 15/898,273, filed on Feb. 16, 2018, now Pat. No. 10,662,457, which is a division of application No. 15/010,528, filed on Jan. 29, 2016, now Pat. No. 9,908,064.

(60) Provisional application No. 62/151,086, filed on Apr. 22, 2015, provisional application No. 62/112,741, filed on Feb. 6, 2015.

(51) Int. Cl.
| | |
|---|---|
| *C12P 21/00* | (2006.01) |
| *B01D 15/34* | (2006.01) |
| *B01D 15/36* | (2006.01) |
| *B01D 15/38* | (2006.01) |
| *C12N 9/12* | (2006.01) |
| *C07K 14/505* | (2006.01) |
| *C07K 14/535* | (2006.01) |
| *C12M 1/40* | (2006.01) |
| *C12M 1/00* | (2006.01) |
| *C12M 1/36* | (2006.01) |
| *C12M 3/00* | (2006.01) |
| *B01D 15/12* | (2006.01) |
| *B01D 15/10* | (2006.01) |
| *B01D 15/14* | (2006.01) |
| *B01D 15/22* | (2006.01) |
| *C12P 21/02* | (2006.01) |
| *C12N 1/06* | (2006.01) |
| *C12P 21/06* | (2006.01) |

(52) U.S. Cl.
CPC .............. *C12P 21/00* (2013.01); *B01D 15/10* (2013.01); *B01D 15/12* (2013.01); *B01D 15/14* (2013.01); *B01D 15/22* (2013.01); *B01D 15/34* (2013.01); *B01D 15/361* (2013.01); *B01D 15/3804* (2013.01); *C07K 14/505* (2013.01); *C07K 14/535* (2013.01); *C12M 21/18* (2013.01); *C12M 23/28* (2013.01); *C12M 23/44* (2013.01); *C12M 29/00* (2013.01); *C12M 41/48* (2013.01); *C12M 47/10* (2013.01); *C12N 1/06* (2013.01); *C12N 9/1223* (2013.01); *C12N 9/1252* (2013.01); *C12P 21/02* (2013.01); *C12P 21/06* (2013.01); *C12Y 207/03002* (2013.01); *C12Y 207/07007* (2013.01)

(58) Field of Classification Search
None
See application file for complete search history.

(56) References Cited

U.S. PATENT DOCUMENTS

| | | | |
|---|---|---|---|
| 6,780,607 B2 | 8/2004 | Choi et al. | 435/68.1 |
| 7,338,789 B2 | 3/2008 | Swartz et al. | 435/71.2 |
| 8,034,581 B2 | 10/2011 | Hara et al. | 435/68.1 |
| 8,357,529 B2 | 1/2013 | Swartz et al. | 435/317.1 |
| 9,908,064 B2 | 3/2018 | Dresios et al. | |
| 2007/0218075 A1 | 9/2007 | Matsuka et al. | |
| 2013/0280797 A1 | 10/2013 | Rao et al. | 435/288.7 |
| 2015/0110836 A1 | 4/2015 | Glanville | |
| 2016/0339078 A1 | 11/2016 | Hamill et al. | |

OTHER PUBLICATIONS

"Epitope Mapping Protocols in Methods in Molecular Biology," vol. 66, G. E. Morris, Ed., 1996.
International Search Report and Written Opinion for PCT Application No. PCT/US19/40210, dated Nov. 25, 2019, 20 pp.
F. Xian, et al., "Peptide Biosynthesis With Stable Isotope Labeling From a Cell-Free Expression System for Targeted Proteomics With Absolute Quantification," Molecular & Cellular Proteomics, vol. 15(8), pp. 2819-2828, 2016.

(Continued)

*Primary Examiner* — Michelle F. Paguio Frising
(74) *Attorney, Agent, or Firm* — Dawn-Marie Bey; Bey & Cotropia PLLC

(57) ABSTRACT

A portable fluidic platform for rapid and flexible end-to-end production of recombinant protein biologics includes a bioreactor system hosting stable and robust cell-free translation systems that is fluidically integrated with modular protein separation functionalities (e.g., size exclusion, ion exchange or affinity chromatography systems) for purification of the cell-free expressed product and which are configurable for process-specific isolation of different proteins, as well as for formulation. The bioreactor utilizes lysates from engineered eukaryotic (e.g., yeast) or prokaryotic (e.g., bacterial) strains that contain factors for protein folding and posttranslational modifications. Combination of various purification modules on the same fluidic platform allows flexibility of re-routing for purification of different proteins depending on specific target requirements. Protein synthesis and purification modules are integrated into self-contained disposable fluidic cartridge that eliminates cross-contamination between runs. The platform allows for flexible production of protein biologics within 24 hours (from DNA to purified product).

20 Claims, 28 Drawing Sheets

Specification includes a Sequence Listing.

(56) References Cited

OTHER PUBLICATIONS

NCBI, "Hypothetical Protein fnb [imported]—*Staphylococcus aureus* (strain N315)," [online], [retrieved Sep. 3, 2019], PIR: H90053, 1 p., Retrieved From the Internet: https://www.ncbi.nlm.nih.gov/protein/25507937?report=genpept.

H. Takeda, et al., "CP5 system, for simple and highly efficient protein purification with a C-terminal designed mini tag," PLOS One 12(5): e0178246, https://doi.org/10.1371/journal.pone.0178246, 18 pp., May 25, 2017.

R. Narumi, et al., "Cell-free synthesis of stable isotope-labeled internal standards for targeted quantitative proteomics," Synthetic and Systems Biotechnology, vol. 3(2), pp. 97-104, 2018.

S. Buus, et al., "High-resolution Mapping of Linear Antibody Epitopes Using Ultrahigh-density Peptide Microarrays," Molecular & Cellular Proteomics, vol. 11(12), pp. 1790-1800, 2012.

Mehlin, C., et al., "Heterologous expression of proteins from Plasmodium falciparum: results from 1000 genes," Mol. Biochem. Parasitol., 148(2), pp. 144-160, 2006.

Oprea, M. and Antohe, F., "Reverse-vaccinology strategy for designing T-cell epitope candidates for *Staphylococcus aureus* endocarditis vaccine," Biologicals, 41, pp. 148-153, 2013.

Kwon, Y-C, Jewett, M. C., "High-throughput preparation methods of crude extract for robust cell-free protein synthesis," Sci. Rep. 5: 8663, DOI: 10.1038/srep08663, 2015.

Spirin, A. S., "High-throughput Cell-Free Systems for Synthesis of Functionally Active Proteins," *Trends Biotechnol.* 22:538-545, 2004.

Gilbert, M. and Albala, J. S., "Accelerating Code to Function: Sizing Up the Protein Production Line," *Curr. Opin. Chem. Biol.* 6:102-105, 2002.

Mei, Q., Frederickson, C. K., Simon, A., et al., "Cell-Free Protein Synthesis in Microfluidic Array Devices," *Biotechnol. Prog.* 23:1305-1311, 2007.

Goerke, Aaron R. and Swartz, James R., "Development of Cell-Free Protein Synthesis Platforms for Disulfide Bonded Proteins," *Biotechnol. Bioeng.* 99:351-367, 2008.

Yang, Junhao, et al., "Rapid Expression of Vaccine Proteins for B-Cell Lymphoma in a Cell-Free System," *Biotechnol. Bioeng.* 89:503-511, 2005.

Yin, Gang, et al., "Aglycosylated Antibodies and Antibody Fragments Produced in a Scalable in Vitro Transcription-Translation System," *MAbs.* 4:217-225, 2012.

Kline et al., "Methods to Make Homogenous Antibody Drug Conjugates," *Pharm. Res.*, PMID:25511917, 2014.

Carlson, E. D., et al., "Cell-Free Protein Synthesis Applications Come of Age," *Biotechnol. Adv.* 30:1185-1194, 2012.

Katzen, F., et al., "The Past, Present and Future of Cell-Free Protein Synthesis," *Trends Biotechnol.* 23:150-156, 2005.

Swartz, Jim, "Developing Cell-Free Biology for Industrial Applications," *J. Ind. Microbiol. Biotechnol.* 33:476-485, 2006.

Zawada, James F., et al., "Microscale to Manufacturing Scale-Up of Cell-Free Cytokine Product—A New Approach for Shortening Protein Production Development jTimelines," *Biotechnol. Bioeng.* 108:1570-1578, 2011.

Shirokov, V.A., et al., "Continuous-Exchange Protein-Synthesizing Systems," *Methods Mol. Biol.* 375:19-55, 2007.

Kim, Dong-Myung and Swartz, James R., "Regeneration of Adenosine Triphosphate From Glycolytic Intermediates for Cell-Free Protein Synthesis," *Biotechnol. Bioeng.* 74:309-316, 2001.

Jewett, M. C. and Swartz, J. R., "Mimicking the *Escherichia coli* Cytoplasmic Environment Activates Long-Lived and Efficient Cell-Free Protein Synthesis," *Biotechnol. Bioeng.* 86:19-26, 2004.

Jewett, Michael C., et al., "An Integrated Cell-Free Metabolic Platform for Protein Production and Synthetic Biology," *Mol. Syst. Biol.* 4, DOI: 10.1038/msb, 2008.

Zawada, J. F. and Swartz, J. R., "Maintaining Rapid Growth in Moderate-Density *Escherichia coli* Fermentations," *Biotechnol. Bioeng.* 89:407-415, 2005.

Schoborg, Jennifer A., et al., "Substrate Replenishment and Byproduct Removal Improve Yeast Cell-Free Protein Synthesis," *Biotechnol J.* 9:630-640, 2014.

Hodgman, C. E. and Jewett, M. C., "Optimized Extract Preparation Methods and Reaction Conditions for Improved Yeast Cell-Free Protein Synthesis," *Biotechnol. Bioeng.* 110:2643-2654, 2013.

Aoki, M., et al., "Automated System for High-Throughput Protein Production Using the Dialysis Cell-Free Method," *Protein Expr. Purif.* 68:128-136, 2009.

Makino, S., et al., "Cell-Free Protein Synthesis Technology in NMR High-Throughput Structure Determination," *Methods Mol. Biol.* 607:127-147, 2010.

Arnau, J., et al., "Current Strategies for the Use of Affinity Tags and Tag removal for the Purification of Recombinant Proteins," *Protein Expr. Purif.* 48:1-13, 2006.

Mei, Qian, et al., "Protein Synthesis in a Device With Nanoporous Membranes and Microchannels," *Lab Chip.* 10:2541-2545, 2010.

Yamamoto, T., et al., "Evaluation of Cell-Free Protein Synthesis Using PDMS-Based Microreactor Arrays," *Anal. Sci.* 24:243-246, 2008.

Murtas, G., et al., "Protein Synthesis in Liposomes With a Minimal Set of Enzymes," *Biochem. Biophys. Res. Commun.* 363:12-17, 2007.

Iskakova, Madina B., et al., "Troubleshooting Coupled in vitro Transcription—Translation System Derived From *Escherichia coli* Cells: Synthesis of High-Yield Fully Active Proteins," *Nucleic Acids Res.* vol. 34, No. 19, e135, 2006.

Brandi, Letizia, et al., "Assays For the Identification of Inhibitors Targeting Specific Translational Steps," *Methods Mol Med.* 142:87-105, 2008.

Chirino, A. J. and Mire-Sluis, A., "Characterizing Biological Products and Assessing Comparability Following Manufacturing Changes," *Nat. Biotechnol.* 22:1383-1391, 2004.

Leader, B., et al., "Protein Therapeutics: A Summary and Pharmacological Classification," *Nat. Rev. Drug. Discov.* 7:21-39, 2008.

Mocini, D., et al., "Structure, Production and Function of Erythropoietin: Implications for Therapeutical Use in Cadiovascular Disease," *Curr. Med. Chem.* 14:2278-2287, 2007.

Metcalf, D., "The Molecular Biology and Functions of the Granulocyte Macrophage Colony Stimulating Factors," *Blood.* 67:257-67, 1986.

Gan, R. and Jewett, Michael C., "A Combined Cell-Free Trancsription-Translation System From *Saccharomyces cerevisiae* for Rapid and Robust Protein Synthe," *Biotechnol. J.* 9:641-651, 2014.

Bundy, B. C. and Swartz, J. R., "Site-Specific Incorporation of p-propargyloxyphenylalanine in a Cell-Free Environment for Direct Protein-Protein Click Conjugation," *Bioconjug. Chem.* 21:255-263, 2010.

Kitamura, T., et al., "Identification and Analysis of Human Erythropoietin Receptors on a Factor-Dependent Cell Line," *Blood* 73:375-380, 1989.

Young, Carissa L., et al., "Recombinant Protein Express and Purification: A Comprehensive Review of Affinity Tags and Microbial Applications," *Biotechnol. J.* 7:620-634, 2012.

Mortimer, R. K. and Johnston, J. R., "Genealogy of Principal Strains of the Yeast Genetic Stock Center," *Genetics,* 113:35-43, 1986.

Walter, P., et al., "The Protein Translocation Machinery of the Endoplasmic Reticulum," *Philos. Trans. R. Soc. Lond. B. Biol. Sci.* 300:225-228, 1982.

Walter, P., et al., "Protein Translocation Across the Endoplasmic Reticulum," *Cell,* 38:5-8, 1984.

Walter, P. and Blobel, G., "Preparation of Microsomal Membranes for Cotranslational Protein Translocation," *Methods Enzymol.* 96:84-93, 1983.

Lajoie, M. J., et al., "Genomically Recoded Organisms Expand Biological Functions," *Science,* 342:357-360, 2013.

Kim, T. W., et al., "Simple Procedures For the Construction of a Robust and Cost-Effective Cell-Free Protein Synthesis System," *J. Biotechnol.* 126:554-561, 2006.

Matsuda, Daiki and Mauro, Vincent P., "Determinants of Initiation Codon Selection During Translation in Mammalian Cells," *PLoS One,* 5:1-13, DOI: 10.1371/journal.pone.0015057, 2010.

Chappell, S. A., et al., "Ribosomal Tethering and Clustering as Mechanisms for Translation Initiation," *Proc. Natl. Acad. Sci. U.S.A.* 103:18077-18082, 2006.

(56) References Cited

OTHER PUBLICATIONS

Ahn, Jin-Ho, et al., "Use of Signal Sequences as an in Situ Removable Sequence Element to Stimulate Protein Synthesis in Cell-Free Extracts," *Nucleic Acids Res.* 35, DOI: 10.1093/nar/gkl917, 2007.

Dayhoff, M. O., "Atlas of Protein Sequence and Structure," vol. 5, National Biomedical Research Foundation, pp. 101-110, 1972.

Dayhoff, M. O., "Atlas of Protein Sequence and Structure," vol. 5, Supplement 2, National Biomedical Research Foundation, pp. 1-10, 1976.

Kigawa, "Cell-Free Protein Preparation Through Prokaryotic Transcription-Translation Methods," In Cell-Free Protein Production: Methods and Protocols, Endo, et al., Methods in Molecular Biology, vol. 607, Humana Press, New York, NY, pp. 1-9, 2010.

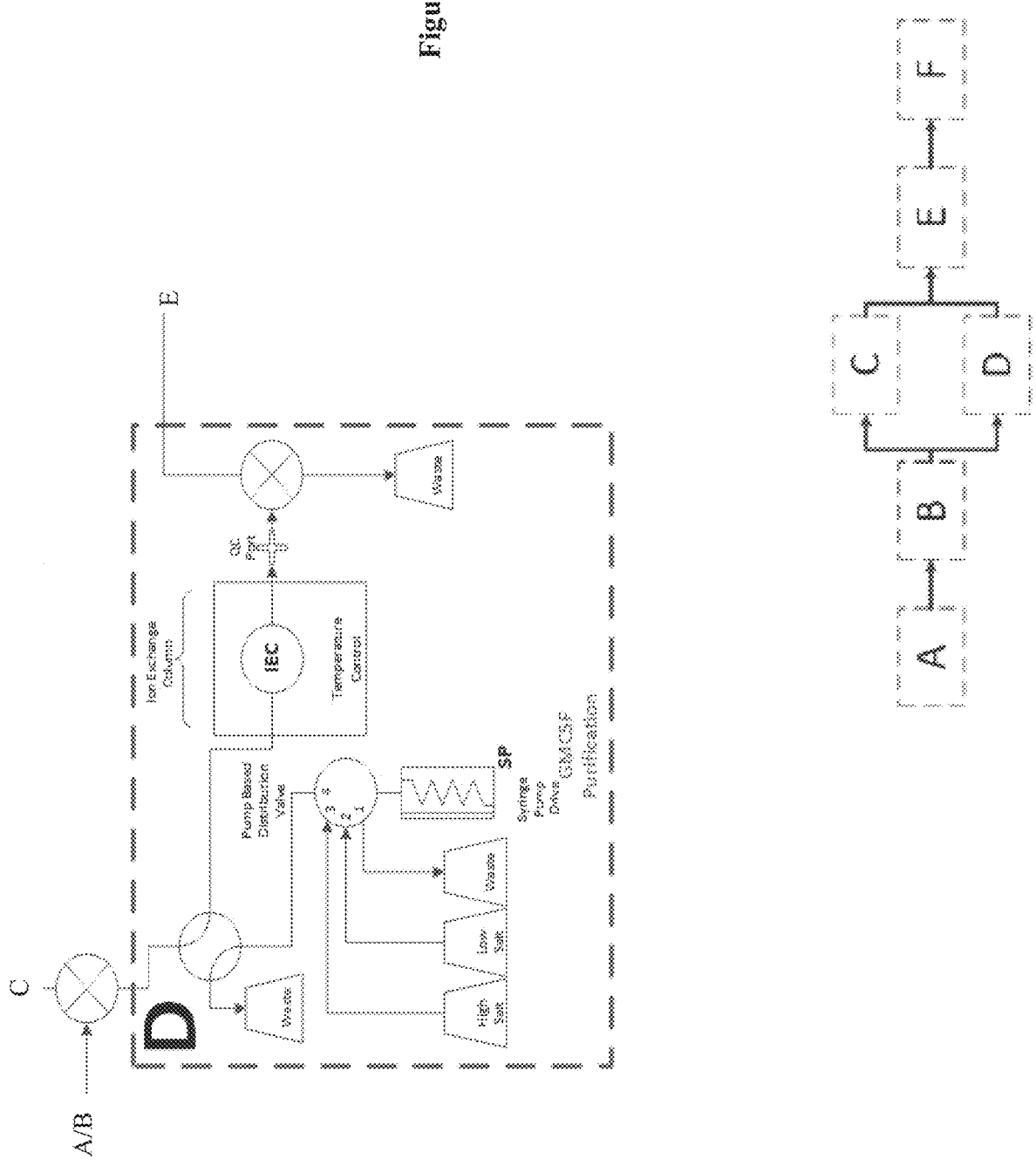

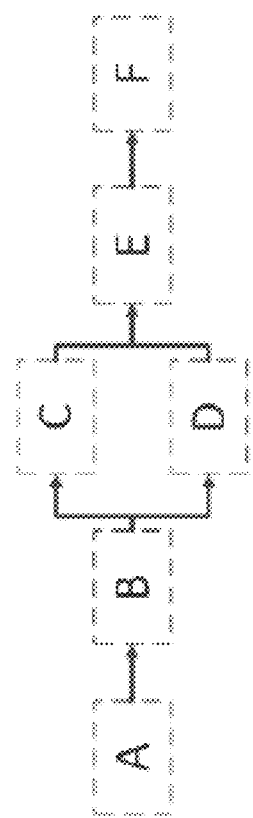
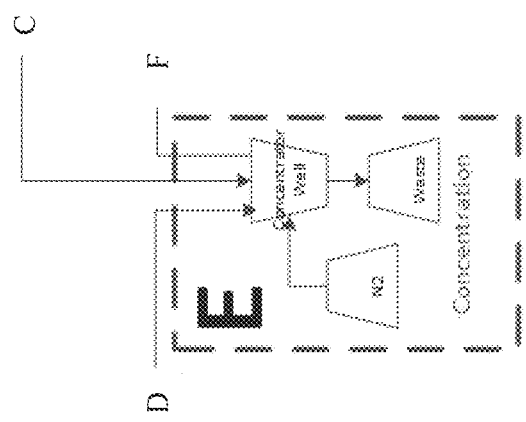
Figure 2E

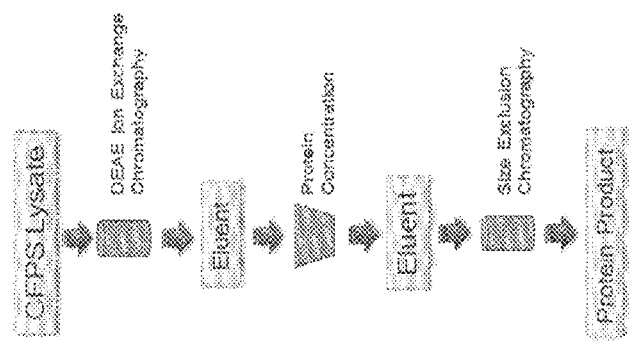
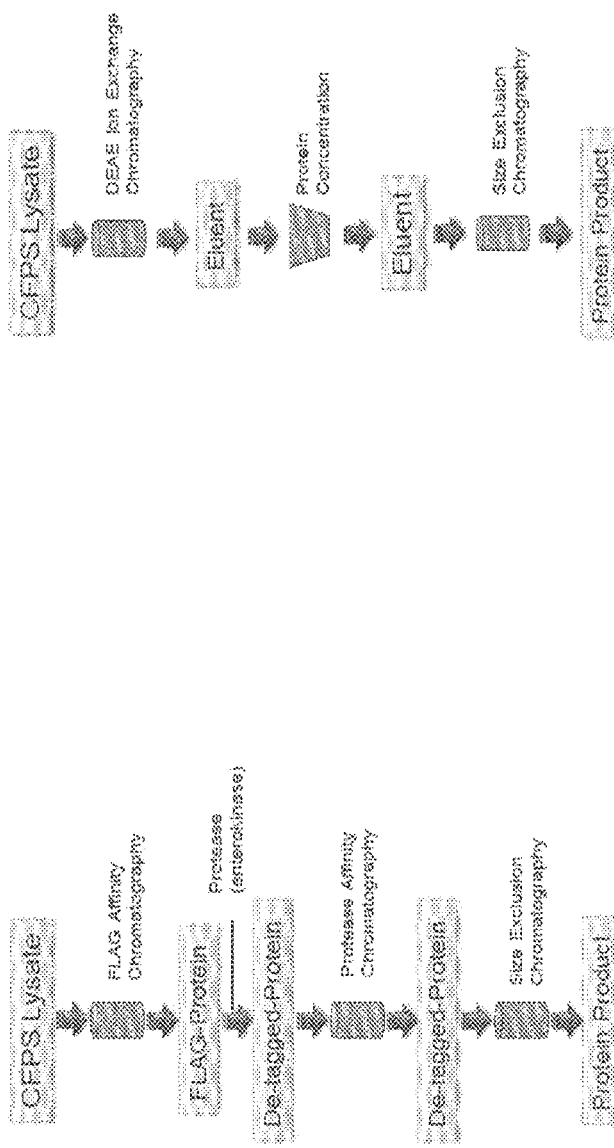
Figure 8

Mass Spectrometry – rhEPO Expressed in the Yeast CFPS System

Results Summary

*Trypsin digest - amino acids matched between expressed rhEPO and expected protein sequence:*
APPR LICDSR VLER YLLEAK EAENITTGCAEHCSLNENITVPDTK VNFYAWK R.MEVGQAVEVWQGLALLSEAVLR GQALLVNSSQPWEPLQLHVDK AVSGLR SLTTLLR ALGAQK EAISPPDAASAAPLR TITADTFR K LFR VYSNFLR GK LK LYTGEACR TGDR

*Glu-C digest - amino acids matched between expressed rhEPO and expected protein sequence:*
APPRLICDSRVLE RYLLE AKE AE.NITTGCAE HCSLNE NITVPDTKVNFYAWKRME VGQQAVE VWQGLALLSE AVLRGQALLVNSSQPWEPLQLHVDKAVSGLRSLTTLLRALGAQKE AISPPDAASAAPLRTITADTFRKLFRVYSNFLRGKLKLYTGEACRTGDR

*144 of 166 (86.7%) amino acids of expressed rhEPO matched expected EPO sequence using overlap between Trypsin and GluC digests:*

APPRLICDSRVLERYLLE AK EAENITTGCAEHCSLNENITVPDTKVNFYAWKRMEVGQQAVE VWQGLALLSEAVLRGQALLVNSSQPWEPLQLHVDK AVSGLR SLTTLLR ALGAQK EAISPPDAASAAPLRTITADTFR KLFR VYSNFLR GKLK LYTGEACRTGDR

Figure 18

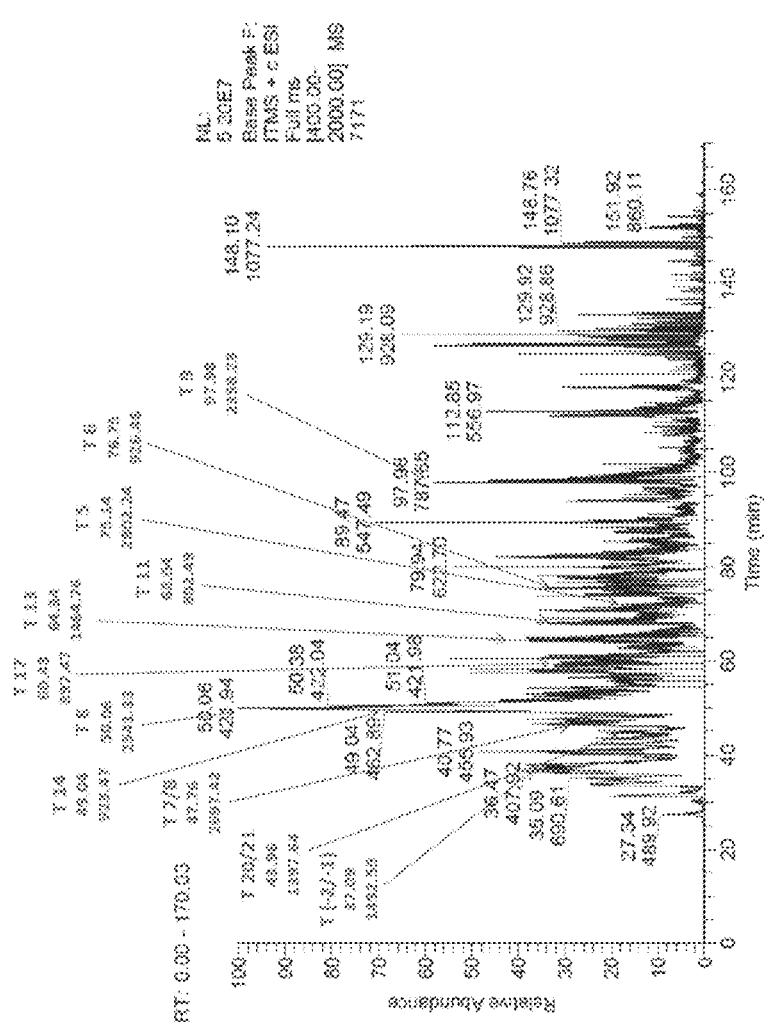
Figure 19: LC-MS/MS analysis of trypsin-digested FLAG–EPO expressed in the yeast CFPS system.

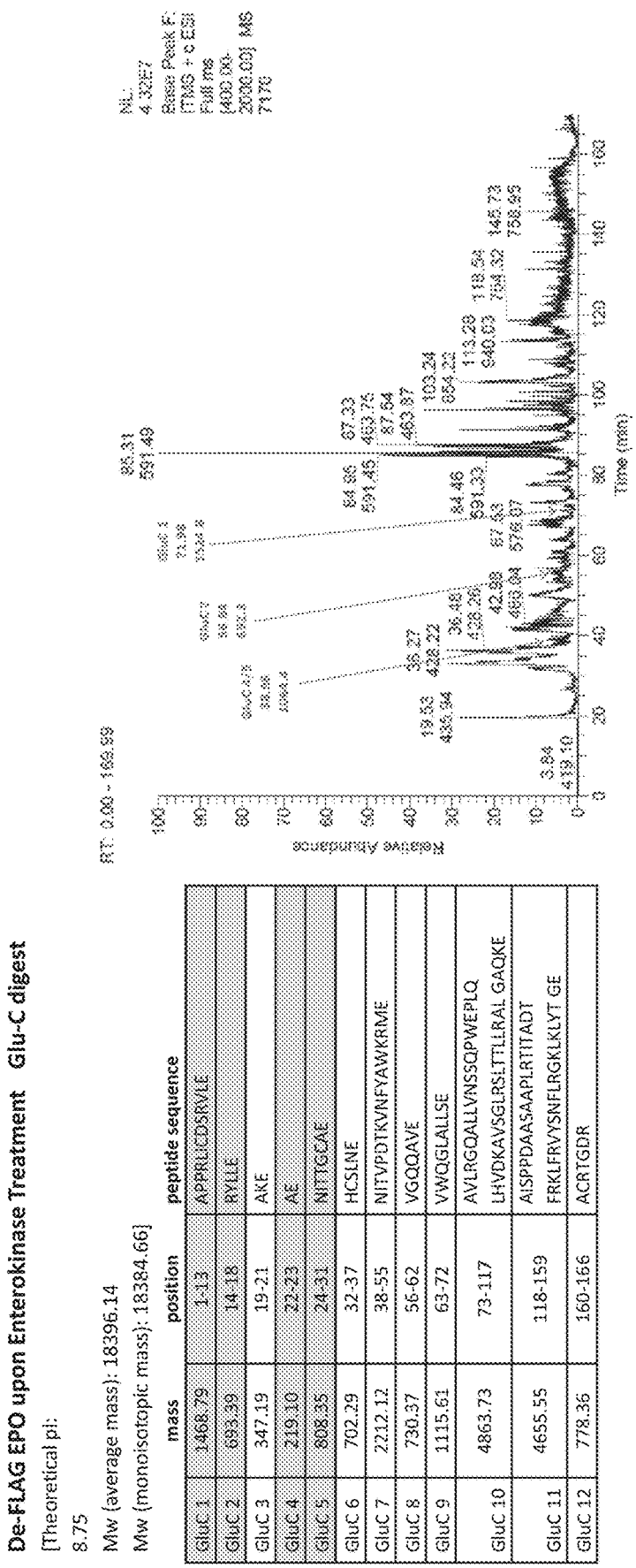
Figure 20: LC-MS/MS analysis of Glu-C-digested de-FLAG-EPO upon enterokinase treatment.

LC-MS/MS sequence analysis of GM-CSF expressed in CFPS system

Results Summary

*Trypsin digest – amino acids matched between expressed rhGM-CSF and expected protein sequence:*

<u>APAR</u> SPSPSTQPWEHVNAIQEALR <u>LLNLSR</u> DTAAEMNETVEVISEMFDLQEPTCLQTR <u>LELYK</u>
<u>QGLR</u> <u>GSLTK</u> <u>LK</u> <u>GPLTMMASHYK</u> QHCPPTPETSCATQIITFESFK <u>ENLK</u> <u>DFLLVIPFDCWEPVQE</u>

*Glu-C digest – amino acids matched between expressed rhGM-CSF and expected protein sequence:*

<u>APARSPSPSTQPWE</u> HNAIQE <u>ALRLLNLSRDTAAE</u> MNE TVE VSE MFDLQEPTCLQTRLE
<u>LYKQGLRGSLTKLKGPLTMMASHYKQHCPPTPETSCATQIITFE</u> SFKE <u>NLKDFLLVIPFDCWEPVQE</u>

*102 of 127 (80.3%) amino acids of expressed rhGM-CSF sequence matched expected GM-CSF sequence using overlap between the two digests:*

<u>APARSPSPSTQPWEHVNAIQEALRLLNLSRDTAAEMNETVEVISEMFDLQEPTCLQTRLELYK</u>
<u>QGLR</u> <u>GSLTK</u> <u>LKGPLTMMASHYKQHCPPTPETSCATQIITFESFK</u> <u>ENLKDFLLVIPFDCWEPVQE</u>

Figure 21

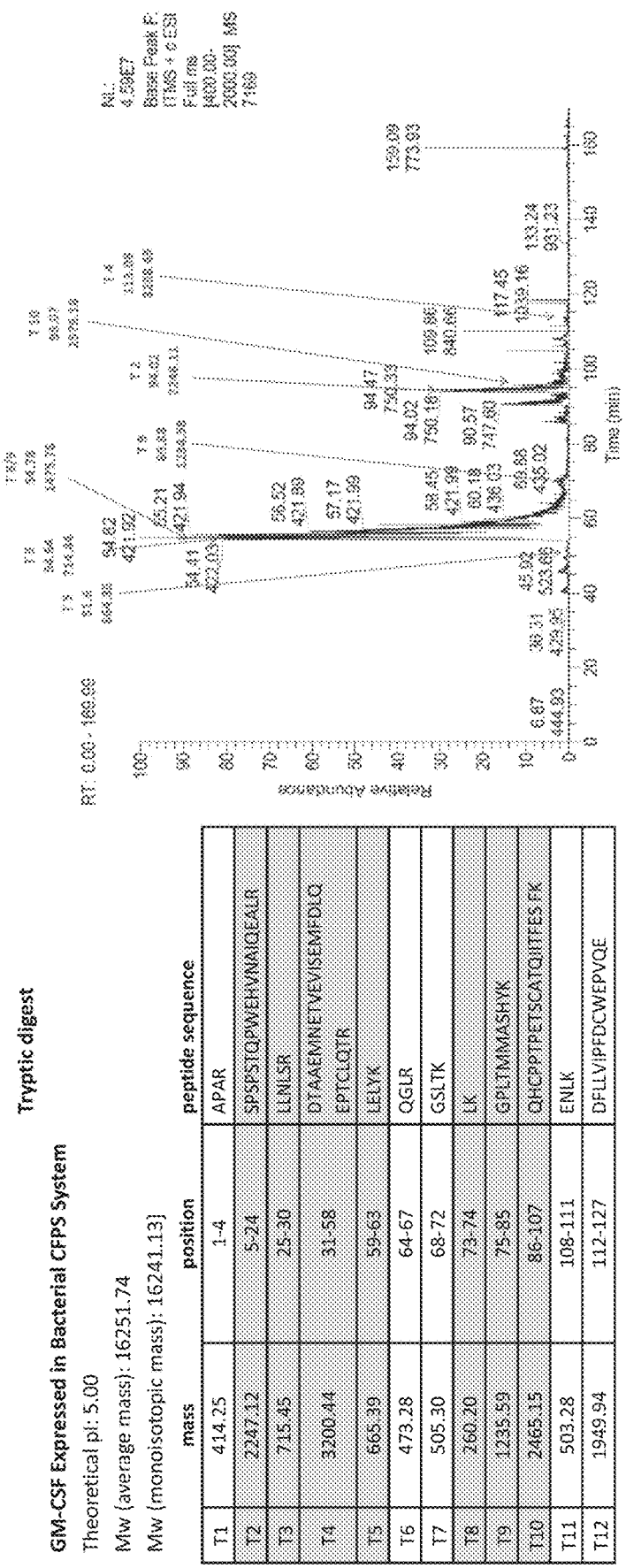
Figure 22: LC-MS/MS analysis of trypsin-digested GM-CSF expressed in the bacterial CFPS system.

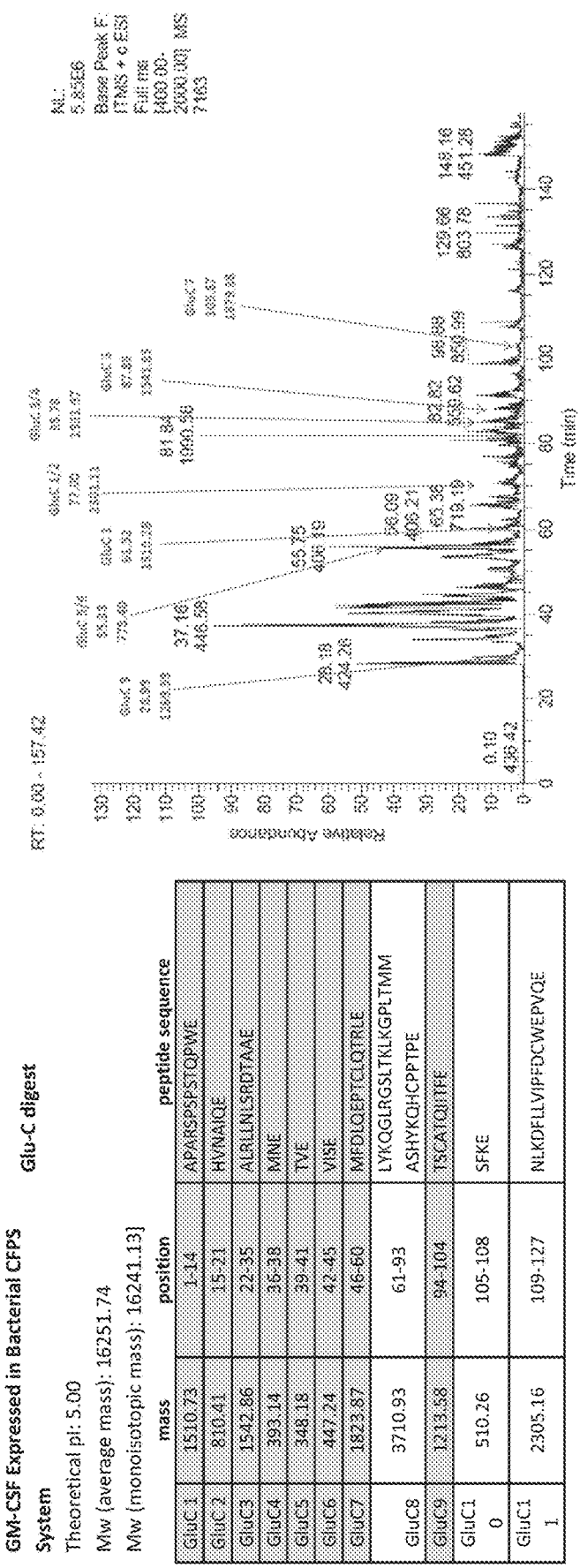
Figure 23: LC-MS/MS analysis of Glu-C-digested GM-CSF expressed in the bacterial CFPS system

SEQUENCE LISTING

```
<160> NUMBER OF SEQ ID NOS: 7

<210> SEQ ID NO 1
<211> LENGTH: 22
<212> TYPE: PRT
<213> ORGANISM: Artificial Sequence
<220> FEATURE:
<223> OTHER INFORMATION: FLAG Synthetic protein sequence tag

<400> SEQUENCE: 1

Asp Tyr Lys Asp His Asp Gly Asp Tyr Lys Asp His Asp Ile Asp Tyr
1               5                   10                  15

Lys Asp Asp Asp Asp Leu
            20

<210> SEQ ID NO 2
<211> LENGTH: 144
<212> TYPE: PRT
<213> ORGANISM: Homo sapiens

<400> SEQUENCE: 2

Met Trp Leu Gln Ser Leu Leu Leu Leu Gly Thr Val Ala Cys Ser Ile
1               5                   10                  15

Ser Ala Pro Ala Arg Ser Pro Ser Pro Ser Thr Gln Pro Trp Glu His
            20                  25                  30

Val Asn Ala Ile Gln Glu Ala Leu Arg Leu Leu Asn Leu Ser Arg Asp
        35                  40                  45

Thr Ala Ala Glu Met Asn Glu Thr Val Glu Val Ile Ser Glu Met Phe
    50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
            100                 105                 110

Cys Ala Thr Gln Ile Ile Thr Phe Glu Ser Phe Lys Glu Asn Leu Lys
        115                 120                 125

Asp Phe Leu Leu Val Ile Pro Phe Asp Cys Trp Glu Pro Val Gln Glu
    130                 135                 140

<210> SEQ ID NO 3
<211> LENGTH: 127
<212> TYPE: PRT
<213> ORGANISM: Homo sapiens

<400> SEQUENCE: 3

Ala Pro Ala Arg Ser Pro Ser Pro Ser Thr Gln Pro Trp Glu His Val
1               5                   10                  15

Asn Ala Ile Gln Glu Ala Leu Arg Leu Leu Asn Leu Ser Arg Asp Thr
            20                  25                  30

Ala Ala Glu Met Asn Glu Thr Val Glu Val Ile Ser Glu Met Phe Asp
        35                  40                  45
```

```
Leu Gln Glu Pro Thr Cys Leu Gln Thr Arg Leu Glu Leu Tyr Lys Gln
 50                  55                  60

Gly Leu Arg Gly Ser Leu Thr Lys Leu Lys Gly Pro Leu Thr Met Met
 65                  70                  75                  80

Ala Ser His Tyr Lys Gln His Cys Pro Pro Thr Pro Glu Thr Ser Cys
                 85                  90                  95

Ala Thr Gln Ile Ile Thr Phe Glu Ser Phe Lys Glu Asn Leu Lys Asp
                100                 105                 110

Phe Leu Leu Val Ile Pro Phe Asp Cys Trp Glu Pro Val Gln Glu
                115                 120                 125

<210> SEQ ID NO 4
<211> LENGTH: 181
<212> TYPE: PRT
<213> ORGANISM: Artificial Sequence
<220> FEATURE:
<223> OTHER INFORMATION: FLAG-EPO recombinantly expressed protein

<400> SEQUENCE: 4

Asp Tyr Lys Asp His Asp Ile Asp Tyr Lys Asp Asp Asp Asp Lys Ala
 1                   5                  10                  15

Pro Pro Arg Leu Ile Cys Asp Ser Arg Val Leu Glu Arg Tyr Leu Leu
                 20                  25                  30

Glu Ala Lys Glu Ala Glu Asn Ile Thr Thr Gly Cys Ala Glu His Cys
             35                  40                  45

Ser Leu Asn Glu Asn Ile Thr Val Pro Asp Thr Lys Val Asn Phe Tyr
 50                  55                  60

Ala Trp Lys Arg Met Glu Val Gly Gln Gln Ala Val Glu Val Trp Gln
 65                  70                  75                  80

Gly Leu Ala Leu Leu Ser Glu Ala Val Leu Arg Gly Gln Ala Leu Leu
                 85                  90                  95

Val Asn Ser Ser Gln Pro Trp Glu Pro Leu Gln Leu His Val Asp Lys
                100                 105                 110

Ala Val Ser Gly Leu Arg Ser Leu Thr Thr Leu Leu Arg Ala Leu Gly
            115                 120                 125

Ala Gln Lys Glu Ala Ile Ser Pro Pro Asp Ala Ala Ser Ala Ala Pro
        130                 135                 140

Leu Arg Thr Ile Thr Ala Asp Thr Phe Arg Lys Leu Phe Arg Val Tyr
145                 150                 155                 160

Ser Asn Phe Leu Arg Gly Lys Leu Lys Leu Tyr Thr Gly Glu Ala Cys
                165                 170                 175

Arg Thr Gly Asp Arg
            180

<210> SEQ ID NO 5
<211> LENGTH: 166
<212> TYPE: PRT
<213> ORGANISM: Artificial Sequence
<220> FEATURE:
<223> OTHER INFORMATION: FLAG-EPO after cleavage of FLAG tag

<400> SEQUENCE: 5

Ala Pro Pro Arg Leu Ile Cys Asp Ser Arg Val Leu Glu Arg Tyr Leu
 1                   5                  10                  15

Leu Glu Ala Lys Glu Ala Glu Asn Ile Thr Thr Gly Cys Ala Glu His
                 20                  25                  30

Cys Ser Leu Asn Glu Asn Ile Thr Val Pro Asp Thr Lys Val Asn Phe
             35                  40                  45
```

```
Tyr Ala Trp Lys Arg Met Glu Val Gly Gln Gln Ala Val Glu Val Trp
    50              55                  60
Gln Gly Leu Ala Leu Leu Ser Glu Ala Val Leu Arg Gly Gln Ala Leu
 65              70                  75                  80
Leu Val Asn Ser Ser Gln Pro Trp Glu Pro Leu Gln Leu His Val Asp
                 85                  90                  95
Lys Ala Val Ser Gly Leu Arg Ser Leu Thr Thr Leu Leu Arg Ala Leu
                100                 105                 110
Gly Ala Gln Lys Glu Ala Ile Ser Pro Pro Asp Ala Ala Ser Ala Ala
            115                 120                 125
Pro Leu Arg Thr Ile Thr Ala Asp Thr Phe Arg Lys Leu Phe Arg Val
        130                 135                 140
Tyr Ser Asn Phe Leu Arg Gly Lys Leu Lys Leu Tyr Thr Gly Glu Ala
145                 150                 155                 160
Cys Arg Thr Gly Asp Arg
                165

<210> SEQ ID NO 6
<211> LENGTH: 21
<212> TYPE: DNA
<213> ORGANISM: Artificial Sequence
<220> FEATURE:
<223> OTHER INFORMATION: forward rhEPO PCR primer

<400> SEQUENCE: 6
gtgattcatt ctgctaacca g                                          21

<210> SEQ ID NO 7
<211> LENGTH: 70
<212> TYPE: DNA
<213> ORGANISM: Artificial Sequence
<220> FEATURE:
<223> OTHER INFORMATION: reverse rhEPO PCR primer

<400> SEQUENCE: 7
tttttttttt tttttttttt tttttttttt tttttttttt tttttttttt gttagcagcc   60
ggatctcagt                                                          70
```

PORTABLE FLUIDIC PLATFORM FOR RAPID CELL-FREE PRODUCTION OF PROTEIN BIOLOGICS

CROSS REFERENCE TO RELATED APPLICATIONS

The present application is a division of U.S. application Ser. No. 15/898,273, filed Feb. 16, 2018, titled "Portable Fluidic Platform For Rapid Cell-Free Production of Protein Biologics," which is a division of U.S. application Ser. No. 15/010,528, filed Jan. 29, 2016, titled "Portable Fluidic Platform For Rapid Cell-Free Production of Protein Biologics," which claims the benefit of priority to similarly titled U.S. Provisional Application Nos. 62/112,741 and 62/151,086 filed Feb. 6, 2015 and Apr. 22, 2015, respectively. All of the above applications are incorporated herein by reference in their entireties.

STATEMENT REGARDING GOVERNMENT INTEREST

Certain embodiments were made with Government support under Contract Number N66001-13-C-4024 awarded by the Defense Advanced Research Projects Agency. Accordingly, the United States government may have certain rights in those certain embodiments.

REFERENCE TO SEQUENCE LISTING, TABLE OR COMPUTER PROGRAM

A Sequence Listing is being submitted electronically via EFS in the form of a text file, created Jan. 19, 2016, and named "LEID0010UTLseqlist.txt" (6,999 bytes), the contents of which are incorporated herein by reference in their entirety.

TECHNICAL FIELD

The present disclosure relates to a portable platform for production of protein biologics. The integrated fluidic platform encompasses robust, cell-free protein synthesis systems coupled to rapid protein purification and characterization modules enabling production of protein biologics in less than 24 hrs.

BACKGROUND

The safety and efficacy of protein biologics has led to an upswing in the number of such drugs being introduced into development pipelines toward clinical use. Additional benefits of protein drugs will be realized by way of their application for specialized needs that include both precision and personalized medicine, treatment of orphan diseases, and point-of-care delivery of medical products. Currently, the manufacture of protein biologics is primarily implemented with large scale heterologous expression in bacterial, yeast, and mammalian cell-based systems. Problematically, cell-based gene expression and protein folding are host-dependent, and optimization for product export into the culture fluid is often required to improve production. Other limitations of protein production in living cells include: formation of insoluble protein aggregates, protein degradation by intracellular proteases, and in some cases, inadequate target expression due to host cell toxicity of over-expressed protein and/or an inability to confer appropriate humanized post-translational modifications (PTMs) in target proteins. Overall, such cell-based approaches are impractical for cost-effective and rapid manufacture of low doses of protein biologics and/or production at the point of need because they require multiple processes using large bioreactors, specialized facilities, lengthy production cycles, optimum and stable conditions for sustainable cell growth, laborious purification protocols, all resulting in long turnaround times between cell transfection and protein isolation as well as high costs (Spirin 2004, Trends Biotechnol. 22:538-545; Gilbert and Albala, 2002, Curr. Opin. Chem. Biol. 6:102-105; Mei et al., 2007, Biotechnol. Prog. 23:1305-1311).

In vivo protein expression systems also lack robustness and predictability due to their lack of modularity and adaptability to production at the point of need. For at least these reasons, production of proteins for such applications will not be cost effective until there are techniques and systems available to enable production of single doses or small scale made-to-order products for individual needs that meet regulatory criteria for human use.

Cell-free protein synthesis (CFPS) systems have emerged as a powerful cost-effective technology platform for rapid and efficient production of pharmaceutical proteins (Goerke and Swartz, 2008, Biotechnol. Bioeng. 99:351-367; Kanter et al., 2007, Blood. 109:3393-3399; Yang et al., 2005, Biotechnol. Bioeng. 89:503-511; Yin et al., 2012, MAbs. 4:217-225; Kline et al., 2014, Pharm. Res. 2014, PMID: 25511917). CFPS systems have distinct advantages over in vivo methods for recombinant protein production (Carlson et al., 2012, Biotechnol. Adv. 30:1185-1194; Katzen et al., 2005, Trends Biotechnol. 23:150-156; Swartz 2006, J. Ind. Microbiol. Biotechnol. 33:476-485; Zawada et al., 2011, Biotechnol. Bioeng. 108:1570-1578). Cell-free systems are not constrained by ancillary processes required for cell viability and growth (e.g., homeostatic conditions), thereby allowing optimization of production for a single protein product, as well as optimization of protein complexes, incorporation of non-natural amino acids, high-throughput screening and synthetic biology. The absence of a cell membrane enables real-time monitoring, rapid sampling, purification, and direct manipulation of the protein synthesis process. In addition, the cell-free format avoids the process of cell-line generation, thereby allowing system testing and acceleration of the process/product development pipelines.

However, the current eukaryotic CFPS systems suffer from laborious extract preparation procedures, low and variable product yields, expensive reagents, low protein production rates, small reaction scales, and an unproven track record of expressing complex disulfide bonded or glycosylated proteins.

Recent research advances have led to the production of robust cell-free systems for protein synthesis in high yields. These advances have been achieved by increasing reaction duration via continuous supply of substrates and removal of toxic reaction byproducts by diffusional exchange across a membrane under a continuous exchange cell-free (CECF) format (Shirokov et al., 2007, Methods Mol. Biol. 375:19-55) as well as by activating metabolic networks in vitro for energy production, and improving extract preparation procedures (Kim and Swartz, 2001, Biotechnol. Bioeng. 74:309-316; Jewett and Swartz, 2004, Biotechnol. Bioeng. 86:19-26; Jewett et al., 2008, Mol. Syst. Biol. 4, DOI: 10.1038/msb; Zawada and Swartz, 2005, Biotechnol. Bioeng. 89:407-415; Schoborg et al., 2014, Biotechnol J. 9:630-640; Hodgman and Jewett, 2013, Biotechnol. Bioeng. 110: 2643-2654). Cell-free systems also represent flexible manufacturing platforms that are highly amenable to automated liquid handling.

Automated systems for high-throughput protein production and purification for structural studies have been reported (e.g., Aoki et al., 2009, *Protein Expr. Purif.* 68:128-136; Makino et al., 2010, *Methods Mol. Biol.* 607:127-147). Such systems enable rapid dialysis-mode CFPS and purification using immobilized metal affinity chromatography. However, these robotic platforms are currently non-portable and too large for point-of-care applications. In addition, use of affinity tags for protein purification can lead to products having extra amino acids not present in the natural protein sequence (Arnau et al., 2006, *Protein Expr. Purif.* 48:1-13). Development of microfluidic array devices for continuous-exchange, long-lasting (up to 6 hours) bacterial CFPS have also been reported (Mei et al., 2007, *Biotechnol. Prog.* 23:1305-1311; Mei et al., 2010, *Lab Chip.* 10:2541-2545). In addition, polydimethylsiloxane (PDMS)-based microreactor array chips using bacterial cell-free extracts and having a disposable reaction chamber chip have been demonstrated to be useful for hosting CFPS reactions (Yamamoto et al., 2008, *Anal. Sci.* 24:243-246). These microfluidic systems hold promise for high-throughput protein screening and analysis, but due to their small scale and protein yields are not adequate for production and purification of proteins at pharmaceutical levels.

Other efforts use purified translation systems to construct minimal cells using a bottom-up approach. Multiple groups have demonstrated the ability to activate protein synthesis inside of an artificial liposome to more closely mimic native conditions (Murtas et al., 2007, *Biochem. Biophys. Res. Commun.* 363:12-17). Although such systems hold promise for large-scale protein screening and analysis, they are not adequate for manufacturing protein biopharmaceuticals at pharmaceutically-relevant levels.

Examples of related art include: U.S. Pat. No. 7,338,789 describing methods for in vitro synthesis of biological macromolecules under conditions and in a reaction composition wherein oxidative phosphorylation is activated and protein folding is improved; U.S. Pat. No. 8,357,529 describing methods for the enhanced in vitro synthesis of biological molecules; U.S. Pat. No. 6,780,607 describing methods of production of completely post-translationally modified proteins by combination of cell-free protein synthesis and cell-free co- and post-translational modification in reticulocytes lysates, as well as methods of supplementing those lysates with endoplasmic reticulum, Golgi and plasma membranes obtained from a Chinese Hamster Ovary (CHO) cells; and U.S. Pat. No. 8,034,581 disclosing a method for insect cell-free translation and post-translation glycosylation of target proteins, as well as conditions for cell rupture and preparation of lysates carrying translation factors and factors with glycosylation activity.

SUMMARY

The foregoing examples of the related art and limitations related therewith are intended to be illustrative and not exclusive. Other limitations of the related art will become apparent to those of skill in the art upon a reading of the specification and a study of the drawings.

In one aspect, a portable, modular fluidic platform and method for rapid and flexible end-to-end cell-free expression, purification and formulation of recombinant protein biologics at the µg-mg scale is provided. The platform comprises (a) a front end module that selects one or more reaction reagents (which may include DNA, cDNA or mRNA template, a particular type of lysate, and one or more appropriate buffers) and loads them into a reactor module, (b) a reactor module for protein production under continuous exchange cell-free (CECF) protein synthesis format using prokaryotic or eukaryotic cell lysates; (c) a tandem protein purification and concentration module for separation of the target protein(s) from the lysate mixture; and (d) a module for protein polishing and formulation. The platform incorporates components for mixing, a reaction chamber, and a mechanism for moving reaction material through purification modules, and allows addition and removal of waste materials as required. The portable, modular fluidic platform and method provided herein allow the production, purification and formulation of the protein to be completed within a period of 24 hours. The process is flexible, scalable and amenable to automation for rapid production at the point of need of proteins with significant pharmaceutical, medical, or biotechnological value.

In some embodiments, the platform further comprises one or more of the following options: a control system that allows purification of multiple proteins on the same platform via switching among different chromatography columns depending on target protein modalities; sampling ports that allow for removal of small sample aliquots for quality control and assessment of protein synthesis quality, levels and/or purity; syringe pumps with integrated rotor valves for direction of fluidics between various protein synthesis and purification/formulation modules allowing addition of appropriate solvents and removal of waste stream materials as required; swappable modules; and/or a fluidically integrated protein synthesis and purification module into a self-contained disposable, single-use fluidic cartridge that eliminates any possibility of cross-contamination between runs.

In one aspect, a cross-kingdom heterologous, cell-free translation system and method are provided for in vitro synthesis of protein targets carrying mammalian PTMs. The system comprises (a) a DNA or mRNA template encoding a target protein carrying a signal peptide for mammalian ER-targeting, (b) a yeast or bacterial cell-free translation lysate for translation of exogenously added DNA and/or mRNA; and (c) a mammalian post-translational modification extract comprising signal recognition particles (SRPs) and ER/Golgi microsomes for translocation and processing of the nascent protein.

Additional embodiments of the present platform and method, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present disclosure. Additional aspects and advantages of the present disclosure are set forth in the following description and claims, particularly when considered in conjunction with the accompanying examples and drawings.

Specifically, this disclosure is directed toward a portable fluidic platform for rapid and flexible end-to-end production of recombinant protein biologics. The platform consists of a bioreactor system hosting stable and robust cell-free translation systems that is fluidically integrated with modular protein separation functionalities (e.g., size exclusion, ion exchange or affinity chromatography systems) for purification of the cell-free expressed product and which are configurable for process-specific isolation of different proteins, as well as for formulation. The bioreactor utilizes lysates from engineered eukaryotic (e.g., yeast) or prokaryotic (e.g., bacterial) strains that contain factors for protein folding and posttranslational modifications. Combination of various purification modules on the same fluidic platform allows flexibility of re-routing for purification of different proteins depending on specific target requirements. Protein synthesis and purification modules are integrated into self-contained disposable fluidic cartridge that eliminates cross-contamination between runs. Analytical modules (i.e., capillary electrophoresis, E-PAGE) are integrated into critical checkpoints to sample and monitor the process (e.g., assess protein purity levels and determine potential synthesis- or degradation-related impurities) and facilitate decision making during the production course and prior to product release. Protein yield is determined in-line using label-free methods on a small fraction of the sample. In vitro assays (specific to each target protein) are used in- or off-line to assess activity of the produced protein biologic. The platform allows for flexible production of protein biologics within 24 hours (from DNA to purified product).

The platform can be used in cost-effective production of limited dosages of biologics against rare medical conditions (orphan drugs). In another application, the platform can be used to enable fast (within 24 hours) synthesis and testing of proteins at small doses toward identification of lead molecules during research and development efforts. In another use, the platform can be used to provide on-demand ability to generate medications in areas where those are not available due to refrigeration requirements. In another application, the platform can be used in battlefield medicine to increase medical capabilities of far forward providers and enable specific threat response.

The platform described herein exploits the unique properties of CFPS systems for rapid protein production from DNA templates that do not require cell cultures or insertion of DNA sequences into cells. The expression system can be manipulated and optimized, thus avoiding the unpredictability of living systems. The bioreactor utilizes low cost lysates from engineered eukaryotic (e.g. yeast) and prokaryotic (e.g. bacterial) strains that contain factors for protein folding and posttranslational modifications. The freedom of design afforded by cell-free production enables eukaryotic and prokaryotic lysates to be used interchangeably for expression of difficult protein targets. This flexibility yields a general expression platform that scales from two to hundreds of protein biologics, because different proteins can be expressed preferentially in either eukaryotic or prokaryotic systems by simply changing template DNA input. The platform concept also combines an in-line flexible configuration of posttranslational, purification (e.g. ion exchange, size exclusion and affinity chromatography), formulation and characterization modules for efficient production of active protein biologic depending on target requirements. Integrated system allows flexibility of fluidics rerouting for purification of different target proteins on same platform. Such modularity also offers scalability through parallelization.

BRIEF DESCRIPTION OF THE FIGURES

FIGS. 2A through 2F illustrate fluidic processes used in preparation, concentration, purification and formulation of protein biologics;

FIGS. 8A and 8B illustrate schematic representations of (8A) an affinity-tag approach for purification of a protein product from crude lysates, and (8B) a purification scheme for separation of human GM-CSF from a bacterial cell-free protein synthesis system;

FIG. 18: illustrates Trypsin and Glu-C-digestion peptide products of rhEPO expressed in the yeast CFPS system;

FIG. 19: shows the LC-MS/MS analysis of trypsin-digested FLAG™-EPO expressed in the yeast CFPS system;

FIG. 20: shows the LC-MS/MS analysis of Glu-C-digested de-FLAG-EPO upon enterokinase treatment;

FIG. 21: illustrates Trypsin and Glu-C-digestion peptide products of GM-CSF expressed in the yeast CFPS system;

FIG. 22: shows the LC-MS/MS analysis of trypsin-digested GM-CSF expressed in the bacterial CFPS system; and FIG. 23: shows the LC-MS/MS analysis of Glu-C-digested GM-CSF expressed in the bacterial CFPS system.

BRIEF DESCRIPTION OF THE SEQUENCES

Figure 1:
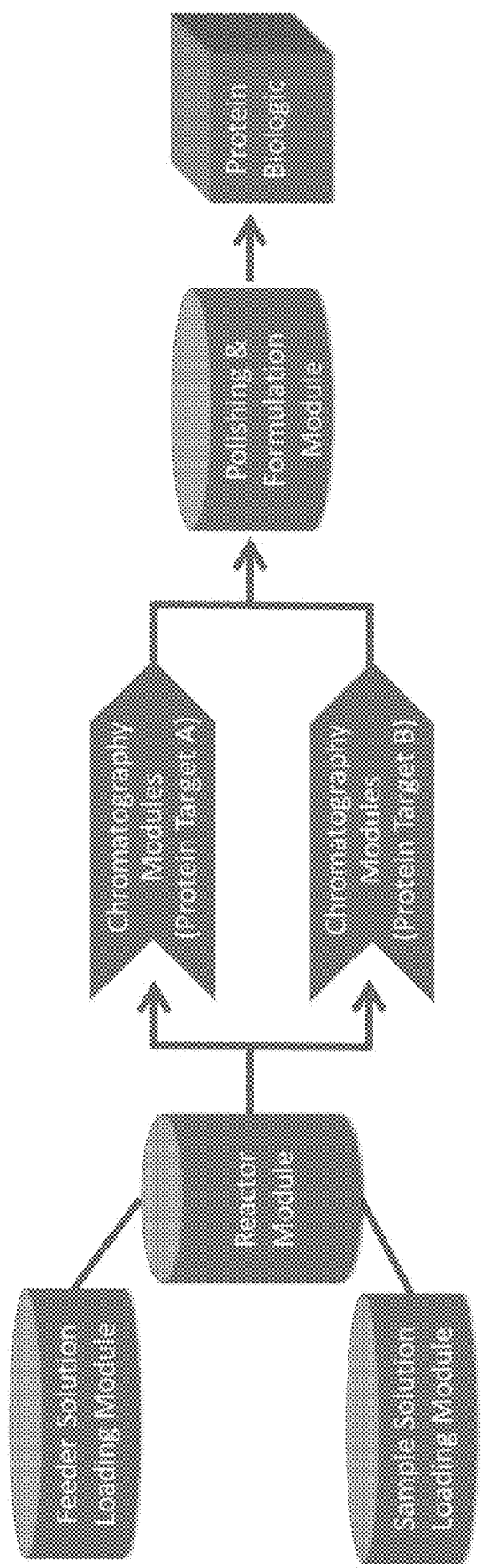
FIG. 1 illustrates a schematic diagram of the fluidic process for cell-free production of protein biologics.
Figure 2A:
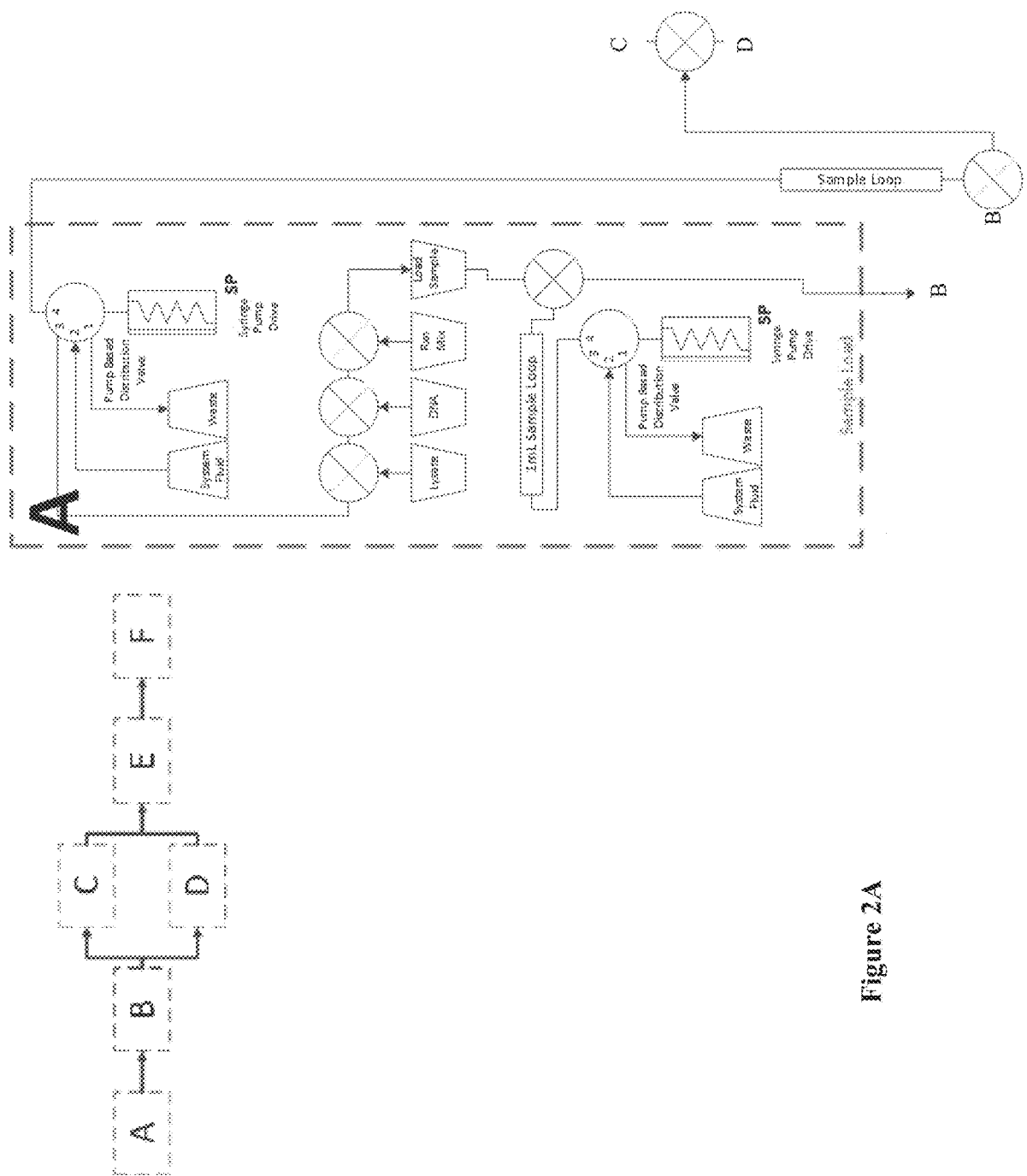
Figure 2B:
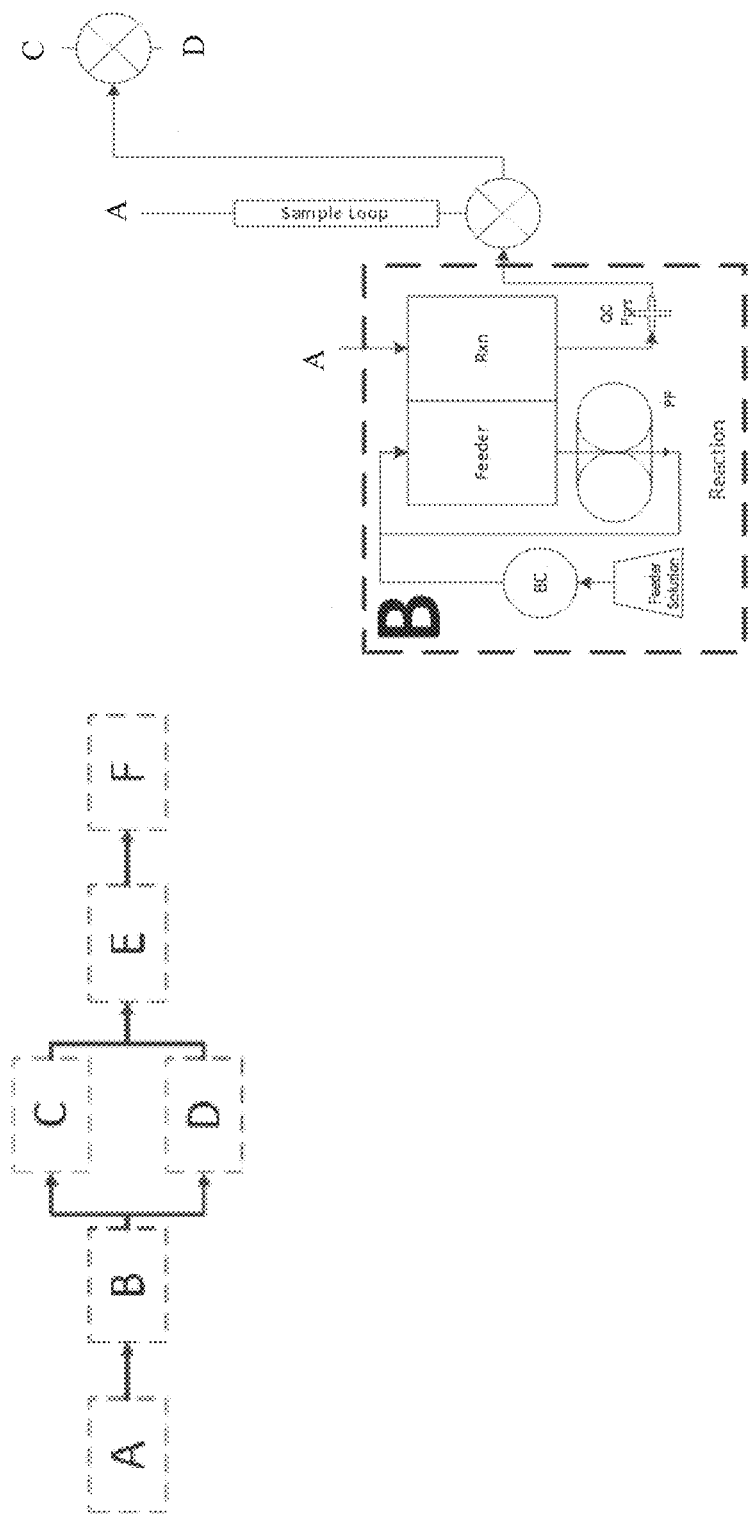
Figure 2C:
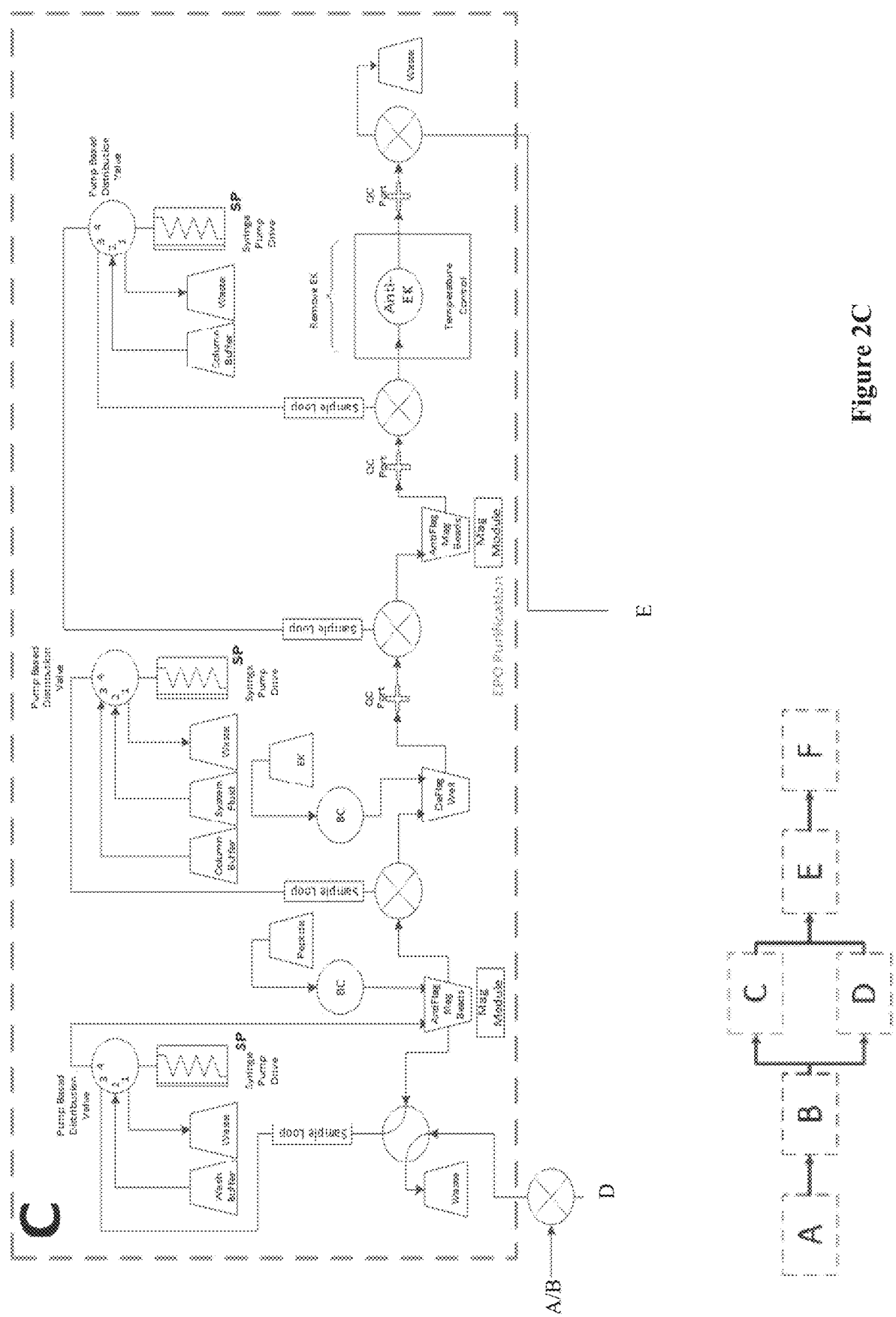
Figure 2F:
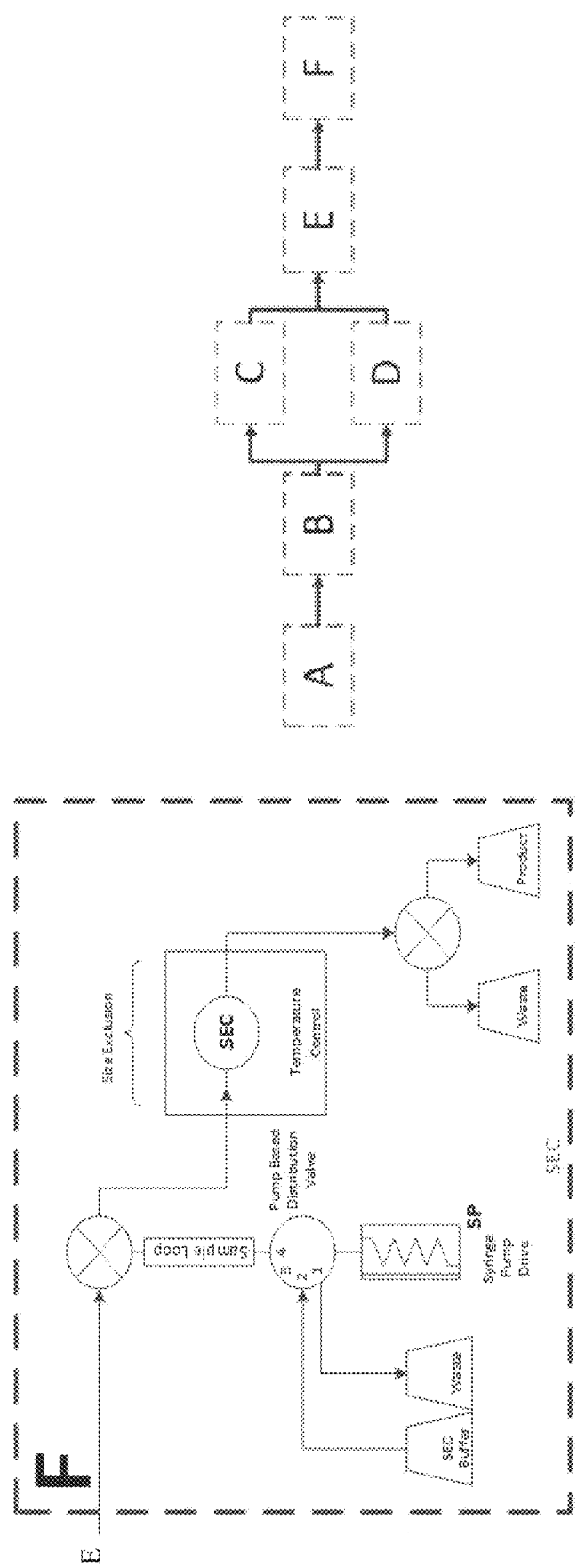
Figure 3:
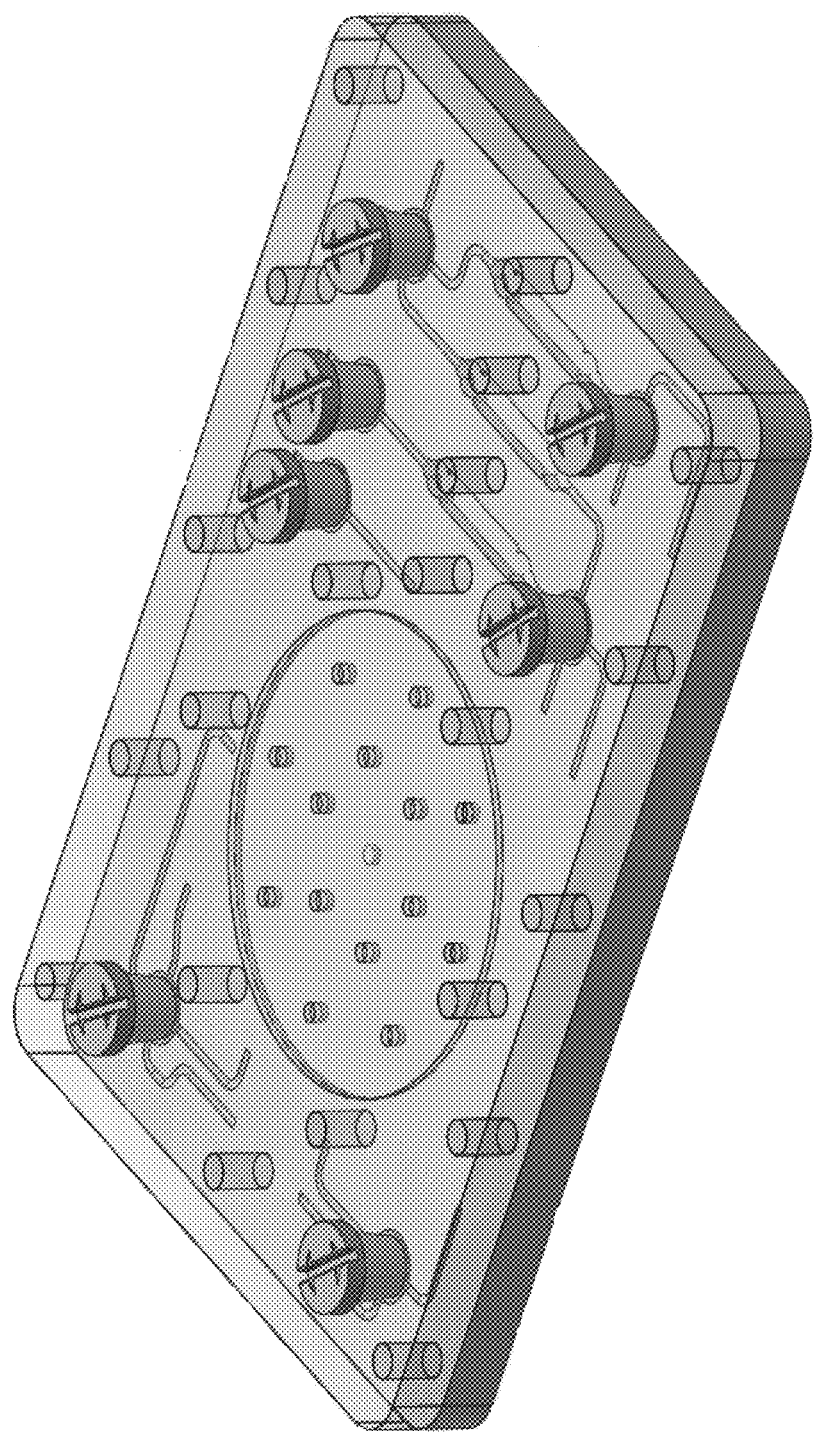
FIG. 3 illustrates a fluidic card for production of protein biologics.

SEQ ID NO: 1 is the amino acid sequence of a triple FLAG™-tag.

SEQ ID NO: 2 is the amino acid sequence of GM-CSF (including signal peptide).

SEQ ID NO: 3 is the amino acid sequence of GM-CSF (without signal peptide).

SEQ ID NO: 4 is the amino acid sequence of FLAG™-EPO.

SEQ ID NO: 5 is the amino acid sequence of EPO (after FLAG™ tag cleavage).

SEQ ID NO: 6 is the forward PCR primer used for generating a template for the expression of rhEPO in yeast.

SEQ ID NO: 7 is the reverse PCR primer used to generate a template for the expression of rhEPO in yeast.

DETAILED DESCRIPTION

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

I. Definitions

As used in this specification and appended claims, the singular forms "a," "an," and "the" include plural referents unless the context clearly dictates otherwise. Thus, for example, reference to "a protein" includes a single protein as well as two or more of the same or different proteins, reference to an "a cell" includes a single cell as well as two or more of the same or different cells, and the like.

As used herein, "protein biologics" refer to protein- or peptide-based products produced by recombinant DNA technology and can include, for example, protein therapeutics, tissue (including blood) protein factors (e.g., factor VIII, thrombolytic agents, hormones, growth factors, interferons and enzymes), vaccines, monoclonal antibodies, and receptor molecules.

As used herein, a "protein of interest" or "POI" is any protein, or functional fragment (such as a protein domain) or derivative thereof, that one skilled in the art wishes to study.

As used herein, the terms "protein" and "polypeptide" are used interchangeably and without distinction to refer to a compound made up of a chain of amino acid residues linked by peptide bonds. Unless otherwise indicated, the sequence for peptides is given in the order from the "N" (or amino) terminus to the "C" (or carboxyl) terminus. It is understood that polypeptides include a contiguous sequence of amino acid residues.

As used herein, the terms "domain" and "region" are used interchangeably herein and refer to a contiguous sequence of amino acids within a protein, typically characterized by being either conserved or variable and having a defined function, such as ligand binding, conferring stability or instability, enzymatic function, etc.

As used herein, "conservative amino acid substitutions" are substitutions that do not result in a significant change in the activity or tertiary structure of a selected polypeptide or protein. Such substitutions typically involve replacing a selected amino acid residue with a different residue having similar physico-chemical properties. For example, substitution of Glu for Asp is considered a conservative substitution since both are similarly-sized negatively-charged amino acids. Groupings of amino acids by physico-chemical properties are known to those of skill in the art.

As used herein, a "variant" protein is a protein having an amino acid sequence that may or may not occur in nature, as exemplified by sequences in GenBank. As used herein, a "mutant" is a mutated protein that may occur in nature, or may be designed or engineered such that its properties (e.g., stability) or functions (e.g., ligand binding) are altered.

A peptide or peptide fragment is "derived from" a parent peptide or polypeptide if it has an amino acid sequence that is homologous, but not identical, to the parent peptide or polypeptide. A peptide may be or represent a fragment of the parent protein or polypeptide.

Two amino acid sequences or two nucleotide sequences are considered "homologous" if they have an alignment score of >5 (in standard deviation units) using the program ALIGN with the mutation gap matrix and a gap penalty of 6 or greater (Dayhoff, M. O., in Atlas of Protein Sequence and Structure (1972) Vol. 5, National Biomedical Research Foundation, pp. 101-110, and Supplement 2 to this volume, pp. 1-10.) The two sequences (or parts thereof) are more preferably homologous if their amino acids are greater than or equal to 50%, 70%, 80%, 90%, 95%, or even 98% identical when optimally aligned using the ALIGN program mentioned above.

A "small molecule ligand" is a discrete small-molecule, well known in the pharmaceutical and material sciences, which is to be distinguished from, e.g., a polypeptide or nucleic acid polymer consisting of monomeric subunits. Small molecule ligands may be naturally-occurring or synthetic as exemplified by pharmaceutical products, laboratory reagents, and the like.

"Modulate" intends a lessening, an increase, or some other measurable change in the stability or biological function of a protein.

As used herein, "preferentially binds" means to bind with greater efficiency to a subject molecule (such as a receptor or other binding partner) than to another molecule. The difference in binding efficiency may be 5-fold, 10-fold, 50-fold, 100-fold, 500-fold, 1,000-fold, 10,000 fold, or more.

As is known in the related art, a "breadboard" is a reusable construction base.

Where a range of values is provided, it is intended that each intervening value, to the tenth of the unit of the lower limit unless the context clearly dictates otherwise, between the upper and lower limit of that range and any other stated or intervening value in that stated range is encompassed within the disclosure. Each smaller range between any stated value or intervening value in a stated range and any other stated or intervening value in that stated range is also encompassed. The upper and lower limits of the smaller ranges may independently be included or excluded in the range, and each range where either, neither or both limits are included in the smaller ranges is also encompassed within the embodiments, subject to any specifically excluded limit in the stated range. Where the stated range includes one or both of the limits, ranges excluding either or both of those included limits are also included in the embodiments. For example, if a range of 1 μl to 8 μl is stated, it is intended that 2 μl, 3 μl, 4 μl, 5 μl, 6 μl, and 7 μl are also explicitly disclosed, as well as a range of 2 μl to 7 μl, as is the range of values greater than or equal to 1 μl and the range of values less than or equal to 8 μl.

In some embodiments, a portable, modular platform for cell-free production, purification and formulation of a protein is provided. In some embodiments, the platform comprises a loading module for loading one or more reaction reagents to a reactor module; a reactor module comprising at least one of prokaryotic and eukaryotic cell lysate mixtures, wherein said reactor module receives the one or more reaction agents from the loading module, and wherein said reactor module facilitates production of a target protein via a process selected from: (i) continuous exchange cell-free (CECF) or (ii) batch protein synthesis; a chromatography module for separating the target protein from the lysate mixtures; and a finishing module for polishing and formulation of the target protein; wherein the production, separation and formulation of the target protein are completed within a period of 24 hours.

In some embodiments, the production, separation and formulation of the target protein are completed within a period of 12 hours. In some embodiments, the production, separation and formulation of the target protein are completed within a period of 10 hours.

In some embodiments, the reactor module comprises a 2 ml polydimethylsiloxane (PDMS) chamber. In some embodiments, the reactor module holds a reaction volume between 0.1 and 5 ml. In some embodiments, the reactor module consists of a 2 ml PDMS chamber divided by a 3.5 kDa dialysis membrane into reaction and feeding chambers holding 1 mL each.

In some embodiments, the loading module includes a feeder solution and a sample solution (also known herein as a reaction solution). In some embodiments, the finishing module includes formulation via a size exclusion chromatography matrix. In some embodiments, the chromatography module for separating the target protein employs at least one of (a) FLAG™-tag-based affinity chromatography, (b) protease affinity chromatography, and (c) size exclusion chromatography steps, or a combination thereof. In some embodiments, the chromatography module for separating the target protein employs at least one of (a) ion-exchange chromatography, (b) protein concentration, and (c) size exclusion chromatography steps, or a combination thereof.

In some embodiments, the lysates comprise a eukaryotic cell-free protein synthesis system. In some embodiments, the lysates comprise a prokaryotic cell-free protein synthesis system.

In some embodiments, the platform comprises cell-free co- and post-translational modification using mammalian (including CHO cell and reticulocyte) lysates.

In some embodiments, the platform further comprises a control system for facilitating purification of different proteins on the same platform via switching among various chromatography matrices. In some embodiments, the platform further comprises one or more sampling ports for removing sample aliquots for assessment of protein synthesis and formulation processes. In some embodiments, the platform further comprises one or more syringe pumps with integrated rotor valves for directing fluidics between one or more modules and allowing addition or removal of a solution. In some embodiments, the platform further comprises a fluidically integrated protein synthesis and purification module into a self-contained disposable fluidic cartridge.

In some embodiments, a heterologous cross-kingdom cell-free translation system for in vitro synthesis of protein targets carrying mammalian PTMs is provided. In some embodiments, the cell-free translation system comprises one or more of a yeast or bacterial cell-free lysate for translation of exogenously added polynucleotide selected from the group consisting of DNA and mRNA; one or more of an exogenous DNA or mRNA template encoding a target protein carrying a signal peptide for mammalian ER-targeting; and a mammalian post-translational modification (PTM) extract comprising signal recognition particles (SRPs), ER and Golgi microsomes, or a combination thereof, for translocation and processing of the target protein(s).

In some embodiments, a method of producing a small amount of a protein biologic formulation at pharmaceutical dosage levels at a point of need using the platform described above is provided, wherein steps of production, separation and formulation of the protein biologic formulation are completed within a period of 24 hours.

In some embodiments, between about 40 µg/ml and about 8 mg/ml protein is produced. In some embodiments, between about 40 µg/ml and about 2 mg/ml protein is produced. In some embodiments, between about 500 µg/ml and about 2 mg/ml protein is produced.

As used herein, a reaction solution is a mixture containing the lysate, polynucleotide template and enzymes and reagents required for DNA transcription and protein synthesis. As used herein, a feeder solution has the same composition as the reaction solution except for the absence of lysate, polynucleotide template and DNA transcription enzyme (for example, T7 polymerase).

This disclosure is directed to a portable fluidic platform for rapid and adaptive cell-free synthesis of multiple protein biologics (FIGS. 1, 2A-2F and 3). In this platform, translationally active lysates—prepared from eukaryotic or prokaryotic cells—are programmed for coupled transcription/translation of an engineered DNA template encoding specific protein targets.

Cell-free protein production offers several advantages over conventional, in vivo, protein expression methods: for example in a cell-free system, most of the subcellular metabolic resources can be directed toward the production of a protein, and the in vitro synthesis environment is more easily controlled absent a cell wall and certain membranous components. Because cell growth or viability are no longer considerations in cell-free protein production systems, conditions such as redox potential, pH, or ionic strength can be altered with greater flexibility than in the case of in vivo protein production. In vitro translation is also recognized for its ability to incorporate unnatural and isotope-labeled amino acids as well as its capability to produce proteins that are unstable, insoluble, or cytotoxic in vivo. Furthermore, components such as tRNA levels can be changed to reflect the codon usage of genes being expressed. Direct recovery of purified, properly folded protein products is readily achieved, and cell-free systems have allowed production of proteins in the mg/ml range.

Regarding a prokaryotic cell-free protein synthesis platform, bacterial *Escherichia coli* provides a suitable source organism since: a) it is an FDA approved microorganism for protein production, b) it allows for inexpensive fermentation in large quantities using low-cost media, c) it has the lowest CFPS reaction cost among other lysates, d) Generates higher protein yields than other lysates, and e) engineered systems enable posttranslational modifications, including S—S and N-linked glycosylation.

Regarding a eukaryotic cell-free protein synthesis platform, yeast *Saccharomyces cerevisiae* can be used as a source organism based on several attractive features, such as: a) it is an FDA-approved microorganism for protein production, b) it provides inexpensive and scalable methods for cell cultivation and lysate production, c) its genome is well characterized genome and there are advanced techniques for its genetic manipulation, and d) it is suitable for synthesis of complex proteins and glycosylation patterns.

The platform disclosed herein allows using both *E. coli* and *S. cerevisiae* CFPS systems to capitalize on the advantages of each platform for expression and manufacture of different protein biologics with varying requirements for expression, PTM, folding kinetics, and scale requirements, such as quantity/therapeutic dose. The flexibility of the platform also allows use of other CFPS systems originating from eukaryotic (e.g., mammalian, plant, insect) or prokaryotic (e.g., archaea or bacterial) organisms. Using methods that are amenable to a fully automated approach, the presently described protein biologics manufacturing platform exemplifies the expression, purification and formulation of two pharmaceutically relevant biologics, recombinant human Erythropoietin (rhEPO) and recombinant human Granulocyte-Macrophage Colony-Stimulating Factor (rhGM-CSF).

Several approaches can be used to maximize protein expression in CFPS systems, such as messenger RNA (mRNA) engineering (e.g., use of strong promoters and/or internal ribosome entry sites), genetic engineering of the source strain(s), and biochemical optimization of the cell-free system(s). Supplementation of these in vitro systems with Endoplasmic reticulum (ER) and Golgi membranes from mammalian cells (e.g. Chinese Hamster Ovary (CHO) cells) allows for synthesis of therapeutically or diagnostically relevant amounts of human biologics carrying appropriate posttranslational modifications for correct folding, high activity and appropriate pharmacological properties. Furthermore, creation of an oxidizing environment that favors disulfide bond formation in target proteins and supplementation of the in vitro system with specific foldases and chaperone molecules allows for correct protein folding and enables synthesis of soluble and active target proteins.

Protein synthesis takes place in bioreactors under batch or CECF formats. An exemplary batch reaction for bacterial CFPS protocols can be performed according to conditions described in Goerke and Swartz (2008, *Biotechnol. Bioeng.* 99:351-367); Iskakova et al. (2006, *Nucleic Acids Res.* 34, e135); or Brandi et al. (2008, *Methods Mol Med.* 142:87-105).

An exemplary continuous exchange reaction for bacterial CFPS protocols can be performed according to conditions described in Shirokov et al. (2007, *Methods Mol. Biol.* 375:19-55).

An exemplary batch reaction for yeast CFPS protocols can be performed as described in Brandi et al. (2008, *Methods Mol Med.* 142:87-105) or Hodgman and Jewett (2013, *Biotechnol. Bioeng.* 110, (10):2643-2654).

An exemplary continuous exchange reaction for yeast CFPS protocols can be performed according to Schoborg et al. (2014, *Biotechnol. J.* 9:630-640).

In the CECF format, bioreactors consist of a dialysis membrane sandwiched between the reaction and feeding chambers, which are made of biocompatible materials. This format allows for replenishment of substrates and removal of low molecular-weight products from the reaction by diffusional exchange across the membrane. CECF systems have been utilized for generation of long-lived, highly-productive in vitro protein synthesis systems using both prokaryotic and eukaryotic lysates.

Various methods can be employed for purification of cell-free produced proteins in the fluidic platform. These methods include use of various chromatographic materials, such as affinity, ion exchange, and size exclusion matrixes. In the case of glycosylated proteins (e.g., erythropoietin), CFPS systems can also be subjected to carbohydrate-affinity chromatography (e.g., lectin-affinity) for specific separation of glycoproteins from the complex lysate according to the structure of their glycan moieties. Quantitative techniques (e.g., colorimetric immunochemical assays or interferometry) can enable determination of protein recovery. Chromatographic techniques can determine purity levels, whereas the mass of the protein and glycosylation sites can be identified by mass spectroscopy. The quality of the final protein sample can be assessed using a series of common protocols in biopharmaceutical manufacturing (Chirino and Mire-Sluis, 2004, *Nat. Biotechnol.* 22:1383-1391).

Integration of the bioreactor with modular functionalities for flexible protein purification, formulation, quantification, activity evaluation and characterization of critical impurities, creates a single, portable platform capable of generating biologically-derived proteins within 24 hours. The system can be designed around self-contained disposable protein synthesis and separation cartridges for elimination of cross-contamination between runs. The cartridges can be temperature stable at ambient temperatures, and individually packaged. In addition, the system can potentially use lyophilized reagents that are hydrated automatically within the device, enabling long-term reagent storage and field use.

Candidate protein biologics produced in the aforementioned platform may include virtually any protein FDA-approved therapeutic (Leader et al., 2008, *Nat. Rev. Drug. Discov.* 7:21-39). One non-limiting example is recombinant human Epoetin alpha, a 166 amino acid glycoprotein (MW~34 KDa) produced by recombinant DNA technology, typically in CHO cells. Epoetin alpha is the recombinant version of endogenous human erythropoietin (EPO; or "rhEPO"), a protein that regulates the production of erythrocytes. Intravenous administration of Epoetin alpha is used to treat anemia caused by renal failure; in addition, it has been shown to have tissue protective, neuroprotective and cardioprotective activity upon injury (Mocini et al., 2007, *Curr. Med. Chem.* 14:2278-2287).

Another non-limiting example is recombinant human Granulocyte-Macrophage Colony-Stimulating Factor (rhGM-CSF), a 143 amino acids (MW~16 kDa) multi-disulfide-bonded cytokine that functions as a white blood cell growth factor and is part of the immune/inflammatory cascade (Metcalf, 1986, *Blood.* 67:257-67). This factor stimulates stem cells to produce granulocytes and monocytes which mature into macrophages and dendritic cells, a process that is crucial for fighting infection.

Another non-limiting example is Hepatitis B Vaccine (purified surface antigen HBsAg) that is currently produced from yeast cultures. Administration of this vaccine reduces incidence of HBV infection and is recommended for military personnel traveling to areas where HBV is endemic.

This disclosure provides cell-free protein synthesis platforms and systems (prokaryotic and eukaryotic) for flexible, scalable, automatable and on-demand expression of a protein biologic at therapeutic dose amounts, wherein the production, purification and characterization process can be completed within 24 hrs. In the platform disclosed herein, the CECF protein synthesis reaction is completed within 12 hours of incubation followed by an additional ~12 hours during which the protein is purified and formulated. In some embodiments, the protein synthesis step can be completed within shorter duration periods (e.g., approximately 2 hours) depending on protein yield requirements. In some embodiments, the purification and formulation process can be completed within shorter duration periods (e.g., approximately 4-8 hours) depending on the protocol requirements for the specific protein target. In some embodiments, the production, purification/separation and formulation processes are completed within a period of 12 hours. In some embodiments, the production, purification/separation and formulation processes are completed within a period of 10 hours.

In the platforms disclosed herein, modular fluidic cartridges were engineered/fabricated and tested for protein synthesis and purification (size exclusion, ion exchange and affinity chromatography). Fluidic reactors for protein synthesis under continuous exchange format were fabricated and tested using 1 and 5 ml reaction volumes. The reactors were implemented with fluidic connectors to allow recirculating flow and fluidic integration with upstream reagents mixing and downstream purification modules. These reactors successfully supported cell free protein synthesis under continuous exchange format, resulting in 8-fold higher yields than batch format, and ~75% yields compared to COTS (Commercial-Off-the-Shelf) CECF reactors, and have been used in end-to-end experiments.

The "end-to-end produced" EPO and GM-CSF protein products were demonstrated to be bioactive, i.e., the EPO and GM-CSF proteins produced in the bioreactor and purified using the chromatographic modules provided herein had similar biological activities to those of commercial control proteins.

Nascent polypeptides synthesized in vitro using the platform/method disclosed herein are soluble and accurately processed enzymatically, resulting in mature proteins with sequences identical to those of pharmaceutical products (Sargramostim™ for GM-CSF and Epogen™ for EPO). Liquid Chromatography-MS/MS confirmed that the N-terminus amino acid sequences of both target proteins are identical to those of the actual pharmaceuticals (i.e., they carry the natural amino acid sequence and do not start with methionine as it is often the case with in vitro expression systems as a means of increasing protein yields).

The nascent polypeptides also bore PTMs: the bacterial cell-free system generated disulfide bonds in the GM-CSF produced, and a fraction of the EPO protein was glycosylated in a reconstituted heterologous system consisting of mammalian ER and Golgi microsomes mixed with either yeast or bacterial lysates.

In some embodiments, it is advantageous to use DNA templates (e.g., plasmids or PCR templates) that carry sequences that enhance protein production in the bacterial CFPS system. Such templates have been successfully used in the platform disclosed herein to accomplish a greater than 50-fold enhancement in protein expression as compared to the previous state of the art methods/systems. For example, human recombinant GM-CSF bearing the sequence of the pharmaceutical product Sargramostim™ was produced at >2 mg per ml of reaction. In addition, by simply changing DNA template, the system allowed production of human recombinant EPO (Epogen™) at >8 mg per ml of reaction.

In some embodiments, it is advantageous to use DNA templates (e.g., plasmids or PCR templates) that carry sequences that enhance protein production in the yeast CFPS system. Such templates have been successfully used in the platform disclosed herein to accomplish a greater than 20-fold enhancement in protein expression as compared to the previous state of the art methods/systems. For example, human recombinant EPO (Epogen™) was produced at ~40 µg per ml of reaction.

A modular strategy for fluidic purification of proteins from prokaryotic and eukaryotic cell-free systems within 12 hrs was developed. Purification yields for GM-CSF and EPO were ~30% and 50%, respectively, allowing generation of single dose amounts of protein products from small cell free reaction volumes (1-5 ml).

Rapid Cell-Free Expression and Purification of Protein Biologics

The process provided herein was developed for rapid production of protein biologics at low doses. The process consists of combined transcription/translation of a DNA template encoding for the target protein under CECF or batch formats followed by a series of purification steps for separation of the protein biologic from the components of the cell-free system. The modularity of this process allows flexibility in using prokaryotic or eukaryotic lysates as well as combination of different protein purification workflows for production of various proteins depending on specific target modalities. This process was used to demonstrate in vitro synthesis and purification of active rhEPO and rhGM-CSF, expressed in S. cerevisiae and E. coli lysates, respectively, in less than 24 hours. These proteins contained the coding sequences for the FDA-approved protein products, Epoetin alfa, a recombinant version of endogenous hEPO, and Sargramostim™, a recombinant version of endogenous hGM-CSF.

Development of a Flexible Process for Production of Protein Biologics

The developed process exploits the unique properties of CFPS systems for rapid protein production from DNA templates that do not require cell cultures or insertion of DNA sequences into cells. Both S. cerevisiae and E. coli CFPS systems were employed to capitalize on the advantages of each platform for expression of different protein biologics with varying requirements. E. coli provides a suitable source organism since it is an FDA approved microorganism for protein production, it allows for inexpensive fermentation in large quantities using low-cost media, it has the lowest CFPS reaction cost among other lysates, and it generates the highest protein yields of all other lysates (Carlson et al., 2012, Biotechnol. Adv. 30:1185-1194). S. cerevisiae was used as a source organism because, similarly to E. coli, it is an FDA-approved microorganism, it provides scalable methods for cell cultivation and lysate production, it is suitable for synthesis of complex proteins, its genome is well characterized and there are advanced techniques for its genetic manipulation. The process described herein affords flexibility and enables S. cerevisiae and E. coli CFPS systems to be used interchangeably for expression of different therapeutics with varying biochemical and pharmacological requirements. As described herein, rhEPO was expressed in the yeast CFPS system whereas rhGM-CSF was produced in the bacterial CFPS system. Parallel experiments showed production of rhEPO in the bacterial CFPS system at yields that were significantly higher than those obtained in the yeast system and similar to those of rhGM-CSF produced in the bacterial CFPS system, and with activities that were comparable to that of a commercially available control EPO protein (results to be described elsewhere). The flexibility of the described process also opens the possibility to use lysates from any organism for such purpose. In addition, reaction volumes in these systems can be scaled up through the use of larger reactors and/or parallelization to allow production of higher doses of protein biologics as needed.

The protein purification principles applied in the present work were focused on utilizing well-characterized resins and established approaches widely used for purification of protein biologics. The modularity of the purification processes, in combination with the flexibility of fluidics routing, can make possible the purification of different proteins on the same platform starting from DNA expressed in their respective CFPS system and continuing through the particular purification scheme optimized for each protein. In addition, complete automation is feasible by putting syringe drives and valves under computer control and the development of robust protocols that reduce/eliminate in-process decisional matrices.

Potential Applications of a Fluidic Process for Rapid Production of Protein Biologics Such a fluidic platform has important applications for the production of protein biologics. Proteins produced in the aforementioned platform may include, for example, FDA-approved protein therapeutics (Leader et al., 2008, Nat. Rev. Drug. Discov. 7:21-39). The system can also be used for rapid, cost-effective, production of limited dosages of biologics against rare medical conditions (orphan drugs), antibody vaccines, or protein-based medical countermeasures. Alternatively, it can be used to enable rapid synthesis and testing of proteins at small doses for drug screening or structure-function analysis during research and development efforts. Furthermore, it can be used for generating medications in areas where those are not available or in military medicine to increase medical capabilities of far forward providers and/or enable specific threat response.

The present disclosure enables production of pharmaceutical-grade proteins by a fully automated portable platform, a capability that could potentially allow reduction of pharmaceutical manufacture to an integrated fluidic process with a single dose lot size. Such a system can produce analytical and statistical data demonstrating that the designed platform can reproducibly deliver a product to an established specification. The process can be optimized by using a Quality-by-Design approach that incorporates appropriate in-process check points and critical quality assurance assays in the final implementation of the manufacturing process to ensure that the limited lot size product meets those specifications. The present disclosure shows that such a platform is feasible for rapid production of low doses of protein biologics at the point-of-need. In addition, the platform is scalable and amenable to integration with fluidic analytical modules towards the generation of a fully automated system for production of proteins with significant pharmaceutical, medical, or biotechnological value.

The following examples are illustrative in nature and are in no way intended to be limiting.

Example 1

DNA Constructs

A plasmid encoding the protein sequence of rhEPO (Epoetin alfa; DrugBank Accession Number DB00016) was generated containing the 5'-UTR fragment of the Omega sequence from the tobacco mosaic virus (Gan and Jewett, 2014, Biotechnol. J. 9:641-651) and used to produce polymerase chain reaction (PCR) DNA templates for combined transcription/translation in the yeast CFPS system. (see FIG. 6).

A plasmid encoding rhGM-CSF (Sargramostim™; DrugBank Accession Number DB00020) was generated from the pY71 backbone (Bundy and Swartz, 2010, Bioconjug. Chem. 21:255-263) for use as a circular DNA template for the bacterial combined transcription/translation CFPS system (see FIG. 11).

Both constructs contained a T7 promoter and signal peptide sequence located upstream of the mature rhEPO and rhGM-CSF coding regions; the rhEPO construct also contained three copies of a FLAG™ epitope located between the signal peptide and the protein coding region for use in an affinity chromatography-based approach for protein purification. Signal peptide and gene sequences were codon modified based on a commercial proprietary method (RESCUE; Promosome, LLC, CA). The PCR templates for the yeast CFPS reactions were generated from the aforementioned rhEPO plasmid using a forward primer with the sequence: 5'-GTGATTCATTCTGCTAACCAG-3' (hereinafter identified as SEQ ID NO: 6), and a reverse primer with the sequence: 5'-$T_{50}$GTTAGCAGCCGGATCTCAGT-3' (wherein "$T_{50}$" means that the first 50 nucleotide residues at the 5' end of the polynucleotide are thymine; the 20 residues following the $T_{50}$ are presented as SEQ ID NO: 7). PCR reactions were performed using Phusion® High-Fidelity DNA Polymerase (New England Biolabs, Inc., MA), 0.2 µM of each primer, and 0.1 ng/µl of template DNA. The PCR product was purified using QIAquick™ PCR Purification Kit (Qiagen, MD), quantified using a NanoDrop™ 1000 (Thermo Fisher Scientific, MA), and its quality assessed by agarose gel electrophoresis.

Example 2

Protein Synthesis Reactor

Figure 4B:
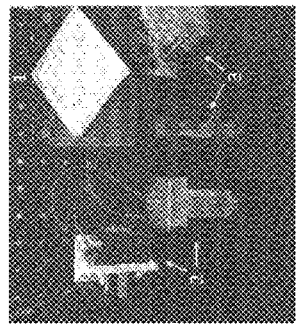
FIGS. 4A and 4B illustrate protein synthesis reactors for continuous exchange protein synthesis.
Figure 4A:
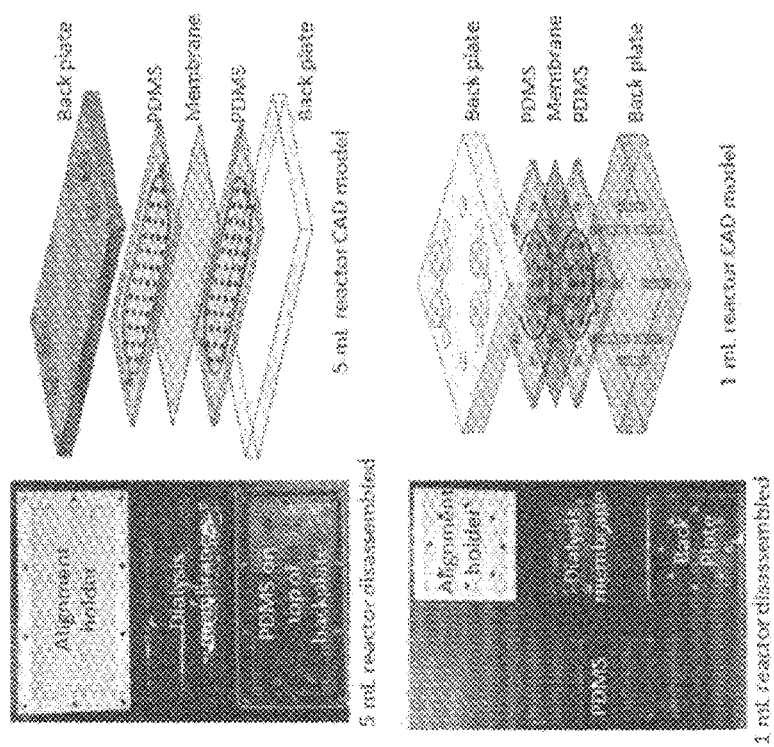
Figure 5:
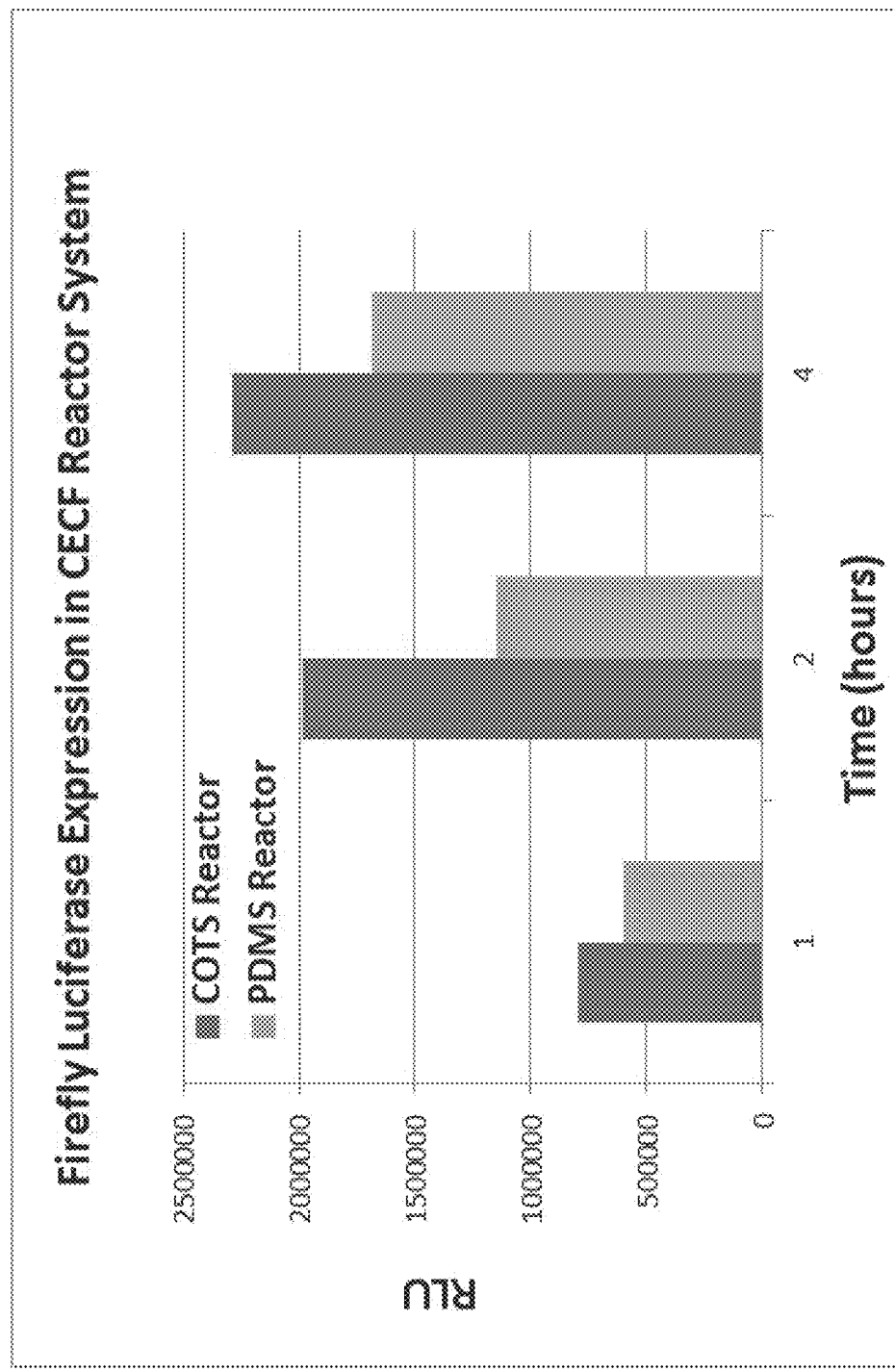
FIG. 5 illustrates protein yield data using a fluidic reactor system.

A computer-aided design model of the protein synthesis reactor for hosting cell free protein synthesis under continuous exchange format is shown in FIG. 4. Dotted features are "stand-off" supports to maintain channel volume by constricting dialysis membrane motion (FIG. 4A). FIG. 4B is a photograph of a protein synthesis reactor, feeder and sample loading modules. The arrow at 1 in FIG. 4B shows a protein synthesis reactor, consisting of a 2 ml polydimethylsiloxane (PDMS) chamber divided into the reaction and feeding chambers (1 ml, each) by a 3.5 kDa molecular weight cut-off regenerated cellulose dialysis membrane (Spectra/Por 7 Dialysis Membrane, VWR, PA). In some embodiments, both halves of the reactor were implemented with 0.010-0.030 ID polyethylene (PE) tubing fluidic systems (Western Analytical Products, CA) to allow for recirculating flow, fluidic integration of the reactor module with the upstream feed and sample reagents modules, and for reaction material recovery. In some embodiments, molded PDMS chambers were produced from a stereo-lithographic printed mold. The arrow at 2 in FIG. 4B shows a peristaltic pump and storage vial for feeder solution loading to the feeding chamber of the reactor and recirculation. The arrow at 3 in FIG. 4B shows a diaphragm and vial for reagents loading to the reactor chamber and sample recovery.

Example 3

Mass Spectrometry

For protein mass spectrometric analysis, protein samples were analyzed in 4-12% SDS-PAGE gels and stained with SimplyBlue SafeStain (Life Technologies Corporation, CA) according to the manufacturer's recommendations. Gel bands migrating to the same molecular weight as the comparative control were excised and mass spectrometry was performed at the facilities of The Scripps Research Institute Center for Mass Spectrometry (TSRI, CA). The gel bands were destained, reduced (10 mM DTT), alkylated (55 mM idoacetamide), and digested with trypsin or Glu-C overnight before being analyzed by nano-LC-MS/MS.

Example 4

Protein Activity Assays

The bioactivity of the purified recombinant human EPO and GM-CSF was assessed using the TF-1 cells proliferation assay; this cell line is derived from bone marrow cells and exhibits growth dependency on both EPO and GM-CSF proteins. (Kitamura et al., 1989, *Blood* 73:375-380). Briefly, TF-1 cells (ATCC #CRL 2003) were maintained in RPMI 1640 media (ATCC 30-2001) supplemented with Fetal Bovine Serum (10%), Penicillin/Streptomycin (100 U/ml) and rhGM-CSF (2 ng/ml), and grown at 37° C. in the presence of 5% $CO_2$. For activity tests, cells were washed three times in growth medium without GM-CSF, plated in 96-well culture plates ($2\times10^4$-$1\times10^5$ cells/ml) in the presence of serial dilutions of the test sample or control protein (final volume 100 µl/well), and incubated at 37° C. for 48-72 hours. At the end of the incubation period, cells were removed from 37° C. and allowed to equilibrate at room temperature for 30 min. An equal volume (100 µl) of room-temperature Cell Titer-Glo reagent (Promega Corporation, WI) was added to the cells followed by shaking of the plates at 900 rpm for two min. After incubation of the plates for 10 min at room temperature, luminescence was measured using a Mithras LB 940 multimode microplate reader (Berthold Technologies, U.S.A. LLC, TN). Human EPO (CYT-201, ProSpec-Tany TechnoGene, Ltd, NJ) and GM-CSF (C003, Novoprotein Scientific, Inc., NJ) proteins were used as controls. Data was analyzed and graphed using GraphPad Prism v6 (GraphPad Software, Inc., CA).

Example 5

Development of a Fluidic Process for Rapid Production of Protein Biologics

A breadboard system was developed for expression, purification and formulation of two separate therapeutic proteins via switching among multiple chromatography columns depending on target protein requirements. Schematic diagrams of the fluidic platform and a fluidic card for production of protein biologics are depicted on FIGS. 1, 2A-2F and 3.

As shown in FIG. 1, the fluidic process consists of: i) Reagents (feeder and reaction/sample solutions) loading to the reactor system, ii) Combined transcription/translation step taking place in a reactor module under continuous exchange or batch format, iii) Protein purification steps for separation of the target proteins from the lysate mixtures using a variety of chromatography matrices depending on protein target modalities, and iv) Protein polishing (i.e., further purification, if/when necessary) and formulation step, typically through the use of a size exclusion chromatography matrix.

The process incorporates a reactor system for CFPS of biologic target proteins using eukaryotic or prokaryotic lysates, modules for protein purification (affinity or ion exchange chromatographies) for isolation of expressed protein from the lysate mixture, and a module for protein polishing (i.e., further purification, if/when necessary) and formulation (size exclusion chromatography) and movement of reaction material through purification modules, with addition and removal of waste materials as required. Temperature control devices can allow independent temperature adjustment of all systems whereas quality control sample ports allow for removal of small aliquot samples for downstream testing. System also allows flexibility of fluidic rerouting for purification of different target proteins (e.g., EPO and GM-CSF) on the same breadboard.

Reactions in batch systems typically plateau after a short period of time (typically 2-3 hours). Potential shortage of critical components, such as amino acids and nucleotides, during protein synthesis, is responsible for such reduction in the rate of protein production over time (Shirokov et al., 2007, *Methods Mol. Biol.* 375:19-55). CECF protein synthesis systems allow replenishment of substrates and removal of low molecular-weight by-products by diffusional exchange across a membrane during protein synthesis (Shirokov et al., 2007, *Methods Mol. Biol.* 375:19-55). Accordingly, a fluidic reactor for protein synthesis under continuous exchange format was fabricated and tested (1 and 5 ml reaction volumes) was developed for supporting CECF protein synthesis. The reactor consists of a conventional regenerated cellulose dialysis membrane sandwiched between the reaction and feeding chambers, which are made of biocompatible materials (PDMS). The reactor is implemented with fluidic connector tubing systems to allow recirculating flow in the feeding chamber, fluidic integration with upstream reagent modules (for possible mixing steps), and sample recovery for downstream purification and processing (FIGS. 4A and 4B). The design allows for use of various and alternative dialysis membrane types with different molecular weight cut-offs for optimum materials exchange as well as further volume scale up through parallel connection of reactor modules depending on yield requirements. The design also allows for direct connection of the two chambers in the absence of a dialysis membrane for supporting CFPS under a batch format. Reactors successfully supported cell free protein synthesis generating ~8-fold higher protein yields than in a batch format and reaching ~75% of the yields obtained in a COTS continuous exchange format reactor.

FIGS. 8A and 8B show schematic diagrams of the fluidic process for cell-free production of protein biologics. FIG. 8A presents a schematic representation of the purification process for recovery of rhEPO from a yeast cell-free protein synthesis system. This method incorporates FLAG™-tag-based affinity chromatography for protein recovery from the cell-free system with subsequent removal of the affinity tag for recovery of the intended size protein target. FIG. 8B presents a process diagram for purification of rhGM-CSF from a bacterial cell-free protein synthesis system via the use of anion-exchange chromatography in combination with size exclusion chromatography.

A modular protein purification strategy was developed for purification of rhEPO from the yeast CFPS system (FIG. 8A). This strategy involves incorporation of three copies of a FLAG™ hydrophilic peptide at the N-terminus of the target protein (see FIG. 6); the FLAG™-tagged protein target can then be purified using an immobilized monoclonal antibody matrix under non-denaturing conditions and eluted by lowering the pH or by adding competing amounts of free FLAG™ peptide. An important feature of the FLAG™ tag is the inherent Enterokinase cleavage site located at the C-terminus of the FLAG™ peptide sequence (Arnau et al., 2006, *Protein Expr. Purif.* 48:1-13; Young et al., 2012, *Biotechnol. J.* 7:620-634). Enterokinase cleaves the FLAG™ epitope without requiring a specific linker sequence and allows for the removal of the tag without leaving residual amino acids on the target protein (Arnau et al., 2006, *Protein Expr. Purif.* 48:1-13; Young et al., 2012, *Biotechnol. J.* 7:620-634). Subsequently, the enzyme can be removed using an Enterokinase-affinity chromatography and the target protein can be recovered and further purified through a size exclusion chromatography step (FIG. 8A). A modular strategy, similar to the method used previously (Zawada et al., 2011, *Biotechnol. Bioeng.* 108:1570-1578), was developed for purification of GM-CSF from bacterial cell-free systems using a combination of ion exchange (DEAE Sepharose Fast Flow) and size exclusion (Sephacryl 5200) chromatography matrices (FIG. 8B).

Example 6

Yeast Cell-Free Protein Synthesis

The rhEPO constructs carrying signal peptide sequences upstream of the coding region as well as a FLAG™ sequence between the signal peptide and the coding region were subjected to coupled transcription/translation in the yeast CECF protein synthesis system. *Saccharomyces cerevisiae* strain S288c (Mortimer and Johnston, 1986, *Genetics*, 113:35-43) was used as the source strain for extract preparation that was performed according to Hodgman and Jewett (2013, *Biotechnol. Bioeng.* 110: 2643-2654) with the exception of growing the yeast cells on synthetic complete media (6.7 g/l Yeast Nitrogen Base (YNB), 20 g/l glucose, 50 mM potassium phosphate buffer, pH 5.5, and 2.002 g/l Synthetic Complete Amino Acids Supplement (ForMedium™, Norfolk, United Kingdom). The yeast CECF combined transcription/translation protein synthesis reaction had the following final composition: 22 mM HEPES, pH 7.4, 120 mM potassium glutamate, 5.5 mM magnesium glutamate, 1.5 mM of each ATP, GTP, CTP, and UTP, 0.08 mM of each of 20 amino acids, 25 mM creatine phosphate, 1.7 mM DTT, 2 mM putrescine, 0.5 mM spermidine, 0.4 mM cAMP, 0.27 mg/ml creatine phosphokinase, 1.3 U/µl T7 polymerase (Thermo Fisher Scientific, MA), 11% glycerol, 6.67 ng/µl PCR amplified DNA template, and 50% (v/v) yeast extract. The feeder solution (present in the feeder chamber of the reactor) had the same composition as the reaction mixture (present in the reaction chamber of the reactor) except for the absence of T7 Polymerase, DNA template, and extract and the presence of 115 mM mannitol. The reaction and the feeder solutions (1 and 10 ml, respectively) were loaded into the CECF reactor and incubated at room temperature for 6 hours with continuous recirculation of the feeder solution at a rate of 1 ml/min. To assess the solubility of the expressed rhEPO in the CFPS system, upon incubation completion, reaction mixtures were centrifuged at 16,000×g for 10 min at 4° C., the supernatant (soluble) fractions were isolated, the pelleted (insoluble) fractions were resuspended in the same volume of phosphate-buffered saline (PBS), and both samples were mixed with SDS loading buffer, heat denatured and subjected to SDS-PAGE followed by Western blot analysis. Unless otherwise specified, reagents were obtained from Sigma-Aldrich Corporation (St. Louis, Mo.). Initial testing of product yields indicated that under these conditions the yeast CFPS system had a variability of approximately 6% between different lysate lots, and variability of less than 5% between replicate experiments using the same lysate lot on different days.

Figure 6:
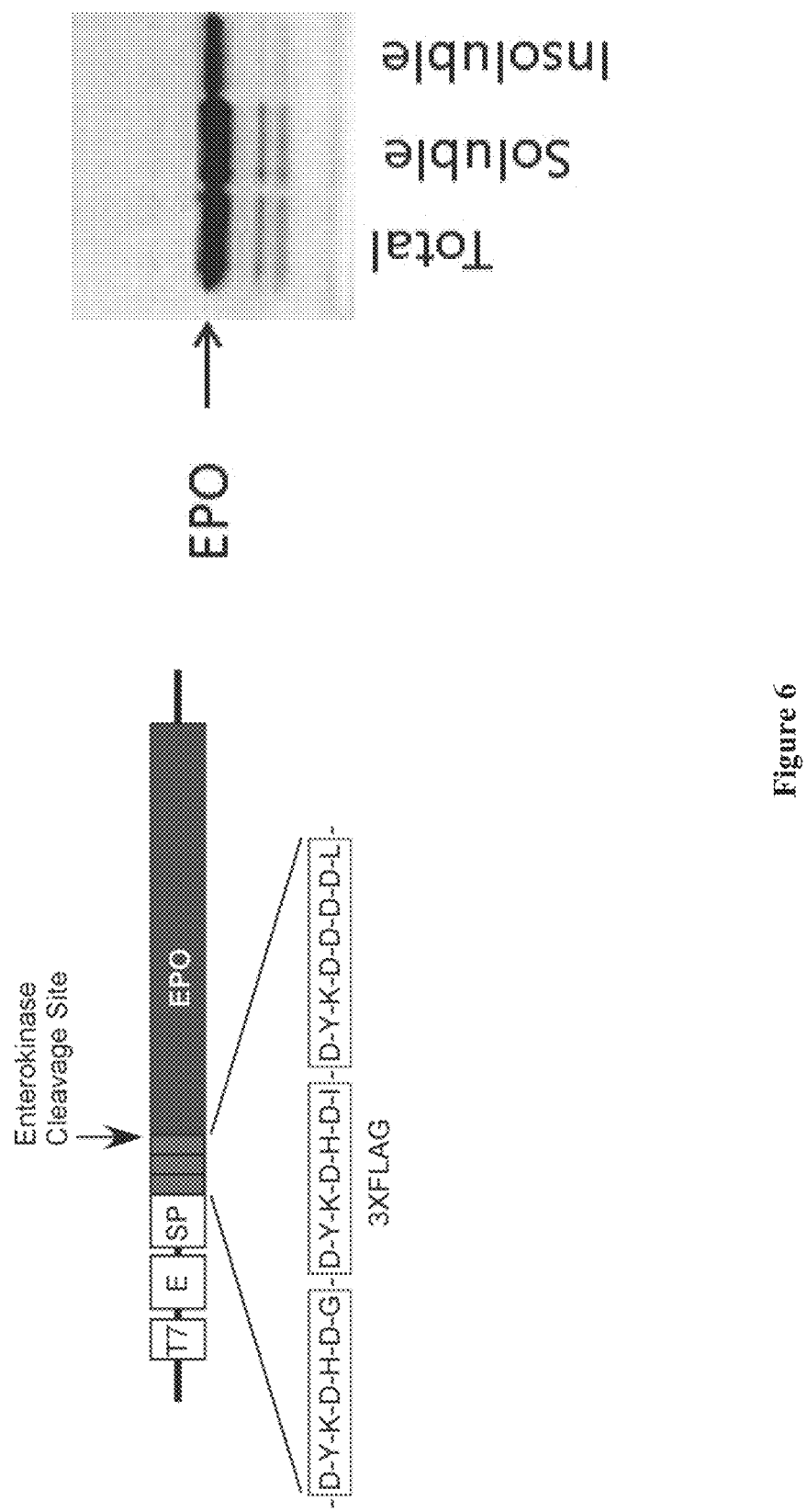
FIG. 6 illustrates expression of human Erythropoietin from an expression plasmid using a yeast cell-free protein synthesis system.

Western blot analysis of the EPO product showed that the expressed protein was present mainly in the soluble fraction (FIG. 6). Nascent polypeptides synthesized in vitro were also accurately processed enzymatically, generating mature proteins with sequences identical to those of the pharmaceutical product (Epogen™). To this end, liquid chromatography-tandem mass spectrometry (LC-MS/MS) confirmed expected target sequences for EPO produced in the yeast system (144 of 166 amino acids were identified (86.7% coverage)). In addition, LC-MS/MS analysis confirmed the presence of the correct N-terminal sequence in the cell-free human EPO protein product as the result of enzymatic affinity tag cleavage during the protein purification process.

Using the yeast CECF protein synthesis system, human EPO was produced at ~40 µg per ml of reaction. Reactions volumes in this system can be scaled up through the use of larger reactors and/or parallelization to allow production of greater amounts and/or higher therapeutic doses of protein biologics, as needed.

Example 7

Glycosylation of Human Erythropoietin in a Heterologous Yeast Cell-Free Protein Synthesis System The cellular posttranslational machinery has been described previously (e.g., Walter et al., 1982, Philos. *Trans. R. Soc. Lond. B. Biol. Sci.* 300:225-228; Walter et al., 1984, *Cell,* 38:5-8). This mechanism involves association of the Signal Recognition Particles (SRPs) with signal peptide (SP) sequences present in newly synthesized proteins destined for the Endoplasmic Reticulum (ER). SRP then carries the ribosome/nascent peptide complex to the ER for binding to the SRP receptor. The nascent protein is inserted into the translocon, translocated into the membrane of the ER, and the SP is cleaved by a peptidase. In the ER, the newly synthesized protein is associated with chaperones for proper folding followed by appropriate post-translational modifications (e.g., glycosylation).

CFPS systems capable of PTMs consist of three main parts: template encoding a target protein carrying a signal peptide for ER-targeting; a lysate capable of translating exogenously added cDNA/mRNA; and SRP and membrane fractions of ER and Golgi microsomes for translocation and processing of the nascent protein. Past efforts have successfully used homologous yeast components (yeast lysate and yeast microsomes) for in vitro synthesis and glycosylation of target proteins as well as heterologous systems made of reticulocyte lysates and microsomes from canine pancreas (e.g., Walter et al., 1982, Philos. *Trans. R. Soc. Lond. B. Biol. Sci.* 300:225-228; Walter and Blobel, 1983, *Methods Enzymol.* 96:84-93; Walter et al., 1984, *Cell,* 38:5-8). However, successful reconstitution of a heterologous cell-free translation system comprising yeast lysate and mammalian microsomes has not yet been demonstrated.

Figure 7:
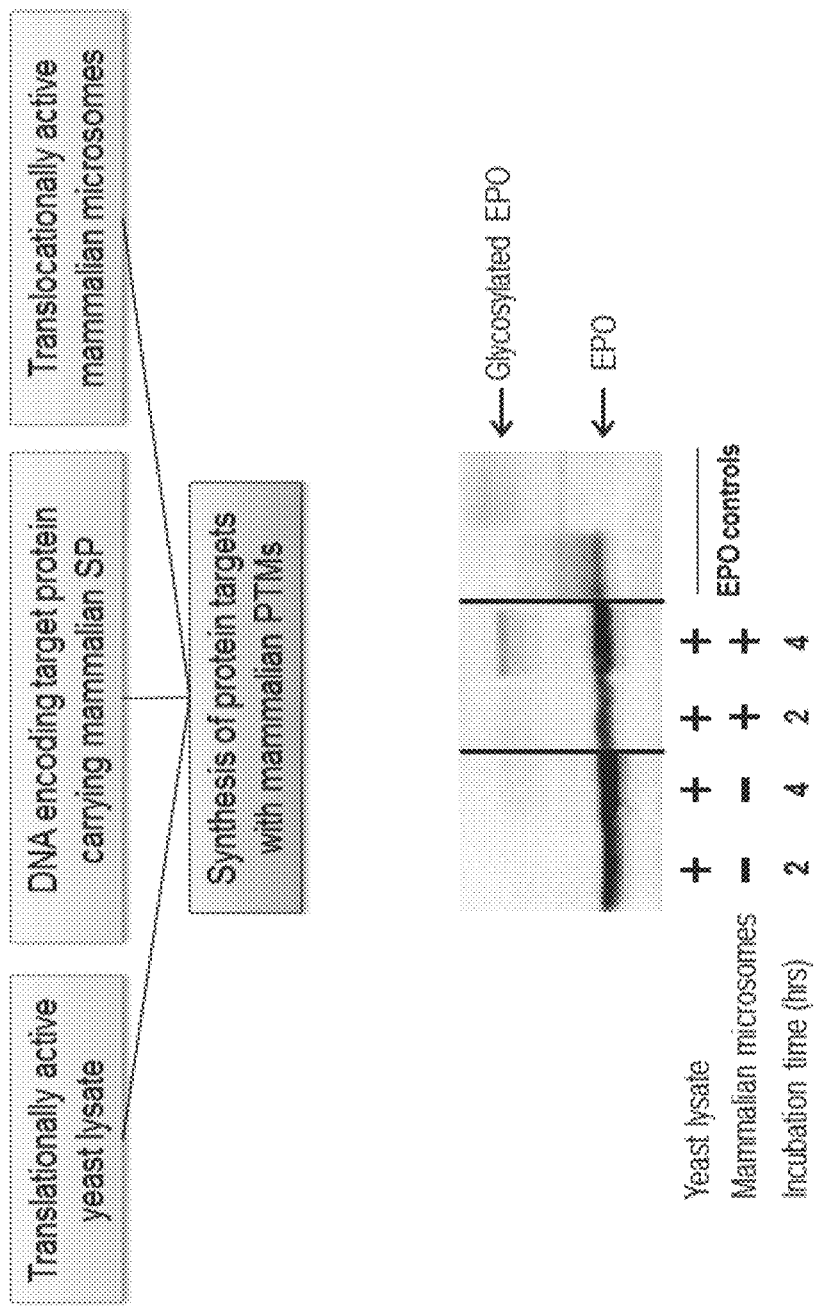
FIG. 7 illustrates in vitro production of human Erythropoietin in a yeast cell-free protein synthesis system combined with the mammalian posttranslational apparatus.

To this end, a heterologous cross-kingdom reconstituted system consisting of a yeast cell-free translation system mixed with the mammalian translocation machinery (ER/Golgi microsomes and SRPs isolated from CHO cells) was developed for in vitro synthesis of protein targets carrying mammalian PTMs. The isolation of mammalian membranes and enzymatic factors was performed using previously described methods (Walter and Blobel, 1983, *Methods Enzymol.* 96:84-93). The results using the aforementioned reconstituted system showed the generation of an EPO protein product having a MW that was similar to that of the glycosylated EPO control protein (FIG. 7).

Example 8

Purification of Human Erythropoietin from a Yeast Cell-Free Protein Synthesis System A modular generalized protein purification strategy was developed for protein purification from a cell-free protein synthesis system (FIG. 8A). This strategy involves incorporation of three FLAG™ tags at the N-terminus of the protein (DYKDDDDL; hereinafter identified as SEQ ID NO: 1 and shown in FIG. 6). FLAG™-tagged proteins can be purified using an immobilized monoclonal antibody matrix under non-denaturing conditions and eluted by lowering the pH or adding competing amounts of free peptide. A unique aspect of FLAG™ is the inherent Enterokinase cleavage site located within the five C-terminal residues of the peptide sequence. Enterokinase cleaves the FLAG™ epitope without requiring a specific linker sequence and allows for the complete removal of the tag without leaving residual amino acids on the target protein. Subsequently, the enzyme can be removed using an Enterokinase-affinity chromatography and the target protein can be recovered and further purified through a size exclusion chromatography.

This strategy was used to purify human EPO from a yeast CECF protein synthesis system (FIGS. 9A through 9D). Purification of expressed FLAG'-tagged rhEPO protein from the yeast lysate was performed using Anti-FLAG® M2 Magnetic Beads (Sigma-Aldrich Corporation, MO) according to the manufacturer's protocol with modifications. Typically this step requires overnight incubation of the protein materials with the beads; however, by increasing the ratio of beads to protein, the binding conditions were optimized and the incubation time reduced to 4 hrs, such that almost all available protein was bound to the beads (FIGS. 9A through 9D). Thus, the magnetic beads were prepared as per the manufacturer's protocol and mixed with the CFPS sample at 1:10 (v/v). Briefly, 5× packed bead volume TBS (50 mM Tris HCl, 150 mM NaCl, pH 7.4) was added and mixed thoroughly with appropriate bead volume. The tube was placed on a magnetic rack and the supernatant was removed followed by one more wash with 5× volume TBS. Lysate was then added to the beads and diluted 3 times with Tris-buffered saline (TBS) (50 mM Tris-HCl, 150 mM NaCl, pH 7.4) in the presence of Tween-20 (0.1%) and, in some embodiments, a protease inhibitor cocktail (Roche cOmplete™ Protease Inhibitor Cocktail Tablets). After incubation and binding at room temperature (≥4 hrs), the affinity captured material was isolated by magnetic bead separation on a magnetic rack and the beads were washed three times with 10 times bead volume TBS. Elution of FLAG™-tag protein was performed using 5× bead volume 0.1M Glycine pH 3.0. The supernatant containing the FLAG™-protein was transferred to a vial containing Tris-HCl pH 8.0 for re-equilibration to neutral pH according to the manufacturer's recommendations (Sigma-Aldrich Corporation, MO).

Figure 9:
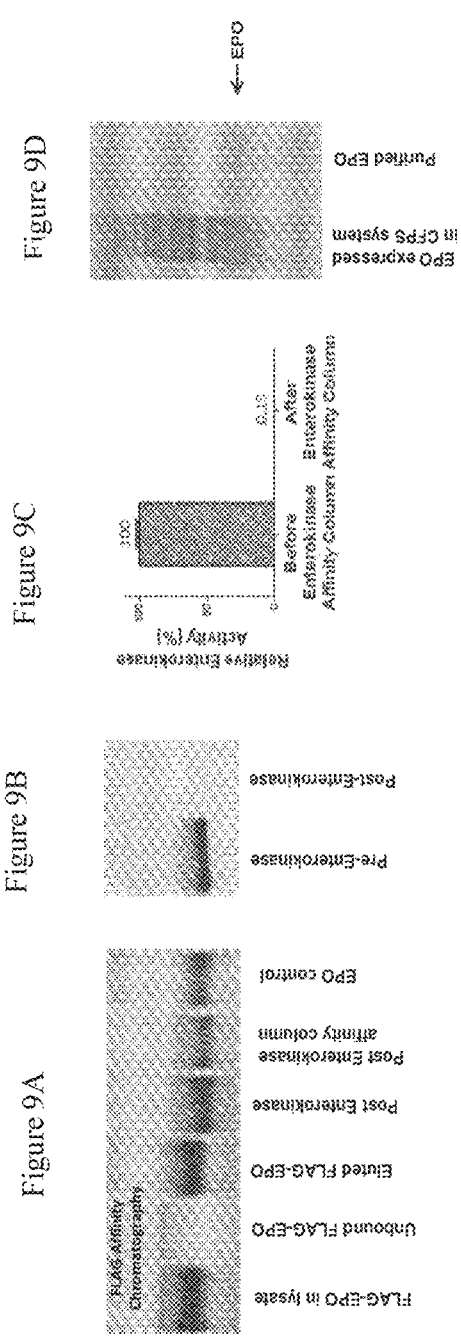
FIG. 9A through 9D illustrates purification data of human Erythropoietin expressed in a yeast cell-free protein synthesis system.

Experiments were also performed to optimize the Enterokinase treatment conditions. Briefly, to remove the FLAG™-tag, eluted FLAG™-protein samples were adjusted to a final concentration of 50 mM NaCl and 2 mM $CaCl_2$), followed by addition of Enterokinase (Novagen, Inc., WI) (1 unit of recombinant Enterokinase per 100 ng FLAG™-protein), and incubation of the mixture at room temperature for 4 hours. Under these conditions, complete cleavage of the FLAG™ epitope from the tagged EPO protein was observed (FIG. 9B). Following cleavage, Enterokinase was removed via affinity-based capture using agarose matrix embedded with soybean trypsin inhibitor according to the manufacturer's protocol (EKapture™ Agarose, Novagen, Inc., MI) according to the manufacturer's protocol. The efficiency of the Enterokinase capture step was assessed using an Enterokinase-specific activity assay (SensoLyte Rh110, AnaSpec, Inc., CA); no observable enzymatic activity remained in the EPO purified sample (FIG. 9C). The de-tagged protein was purified using a 2 ml Sephacryl 5200 HR (GE Healthcare Bio-Sciences, PA) size exclusion chromatography column (ratio 20:1, flow rate of 35 µl/min). Protein samples were analyzed in 4-12% Bis-Tris SDS-PAGE gels with SimplyBlue SafeStain (Life Technologies, Corporation, CA) according to the manufacturer's recommendations. Western blot analyses were performed and preliminary assessment of protein yields during the purification process was performed using yeast cell-free protein synthesis systems spiked in with known amounts of FLAG-EPO followed by protein purification using the resins and buffers described above. Overall purification yields for EPO indicated protein recovery at an estimated 50±5% (FIG. 9A). Thus, the presently disclosed process allows generation of single dose amounts of protein products from small cell free reaction volumes (1-5 ml).

Example 9

Figure 10:
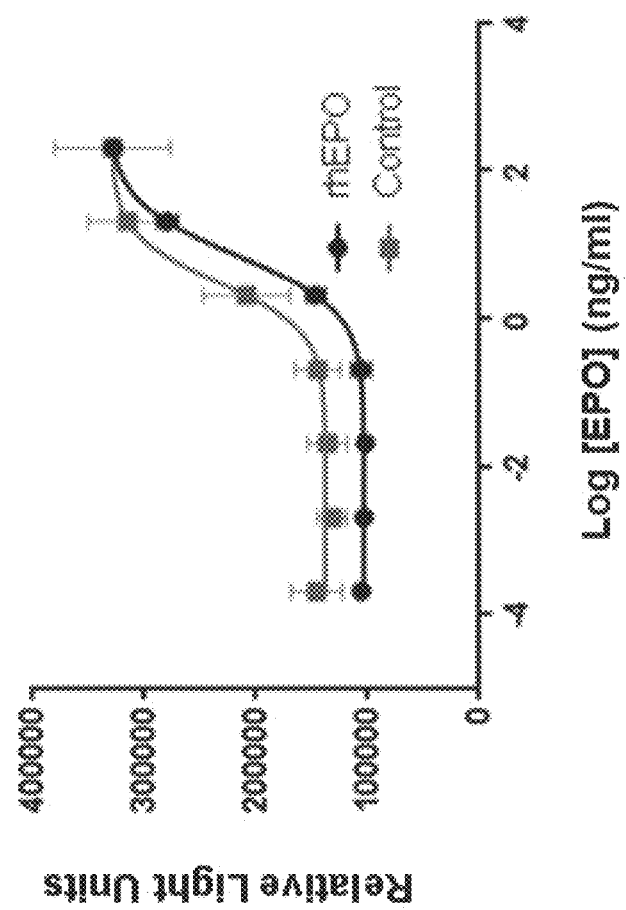
FIG. 10 illustrates bioactivity data of human Erythropoietin protein expressed in a yeast cell-free protein synthesis system and purified using an affinity chromatography system.

Activity of Human Erythropoietin Purified from a Yeast Cell-Free Protein Synthesis System EPO was expressed in a PDMS-based CECF reactor hosting a yeast CFPS system and purified using the FLAG™-affinity chromatography-based protocol as described above. A standard EPO-dependent cell viability assay was employed to determine the bioactivity of the purified protein. This assay is based on quantitation of luminescent signal generated in the presence of ATP, which is directly proportional to the number of metabolically active cells present in the well. Briefly, TF-1 cells (ATCC #CRL 2003) were maintained in RPMI 1640 (ATCC 30-2001) media supplemented with 10% Fetal Bovine Serum, Penicillin/Streptomycin (100 U/ml), 2 ng/ml recombinant Human GM-CSF and grown at 37° C. 5% $CO_2$. Cells were washed three times in growth medium without GM-CSF and plated in 96-well culture plates ($2\times10^4$-$1\times10^5$ cells/ml) in the presence of serial dilutions of sample protein or controls (final volume 100 µl/well). Cells were then incubated at 37° C. for 48-72 hours. At the end of the incubation period, cells were removed from 37° C. and allowed to equilibrate at room temperature for 30 minutes. An equal volume (100 µl) of room-temperature CellTiter-Glo® reagent (Promega) was added to the cells followed by shaking of the plates at 900 rpm for 2 minutes. After incubation of the plates for 10 minutes at room temperature, luminescence was measured. The results showed that end-to-end produced EPO has activity comparable to that of a commercially available and deglycosylated EPO protein (FIG. 10). The EC50 was calculated at 7.469 for the purified EPO expressed in yeast, whereas the EC50 for the EPO control was 3.363.

Example 10

Bacterial Cell-Free Protein Synthesis

Bacterial S30 crude extracts were generated from a genomically recoded release factor 1 (RF1) deficient *E. coli* strain (*E. coli* C321.4Δ.705) (Lajoie, et al., 2013, *Science*, 342:357-360) and described in detail in (Kwon and Jewett, 2015, *Sci. Rep.* 5, DOI:10.1038/srep08663). The bacterial combined transcription/translation protein synthesis reaction was performed in the PDMS reactor under a batch format and had the following final composition: 57 mM HEPES, pH 7.4, 12 mM magnesium glutamate, 10 mM ammonium glutamate, 130 mM potassium glutamate, 1.2 mM ATP, 0.85 mM CTP, 0.85 mM GTP, 0.85 mM UTP, 0.034 mg/ml folinic acid, 0.171 mg/ml tRNA, 2 mM of each of the 20 amino acids, 33.3 mM phosphoenol pyruvate, 0.33 mM NAD, 0.27 mM coenzyme A, 4 mM oxalic acid, 1 mM putrescine, 1.5 mM spermidine, 4 mM glutathione disulfide, 1 mM glutathione, 100 µg/ml disulfide bond isomerase DsbC (Enzo Life Sciences, Inc., NY), 0.1% Brij-35, 1.3 U/μl T7 Polymerase (Thermo Fisher Scientific, MA), 13.3 ng/μl plasmid, and 15% (v/v) E. coli extract. The necessity of addition of exogenous tRNA to the bacterial CFPS reactions was shown previously (Kim, et al., 2006, *J. Biotechnol.* 126:554-561). Prior to use, E. coli extracts were treated with 1 mM iodoacetamide (IAM) (Sigma-Aldrich Corporation, MO) at room temperature for 30 min. The reaction solution was loaded into the reactor and incubated at 30° C. for 10 hours. The solubility of the expressed rhGM-CSF protein was assessed as previously described. Initial assessment of protein yields showed that the bacterial CFPS system had variability of approximately 13% between different lysate lots, whereas variability between replicate experiments using the same lysate lot on different days was less than 5%.

Quantitative assessment of the cell-free rhEPO and rhGM-CSF products was performed using Western blot analysis in the presence of known amounts of protein standards and/or the WES™ system (ProteinSimple, CA). For rhEPO, Western blot analyses were performed using a rabbit anti-EPO antibody (H-162, Santa Cruz Biotechnology, Inc., TX) and a horseradish peroxidase (HRP) conjugated goat anti-rabbit secondary antibody (111-035-003, Jackson ImmunoResearch Laboratories, Inc., PA). For rhGM-CSF, Western blot analyses were performed using a rabbit anti-GM-CSF antibody (AbCam, PLC, MA) and an HRP conjugated goat anti-rabbit secondary antibody (111-035-003, Jackson ImmunoResearch Laboratories, Inc., PA). In both cases, proteins were analyzed using a Storm 840 PhosphorImager (GE Healthcare Bio-Sciences, PA).

Figure 11:
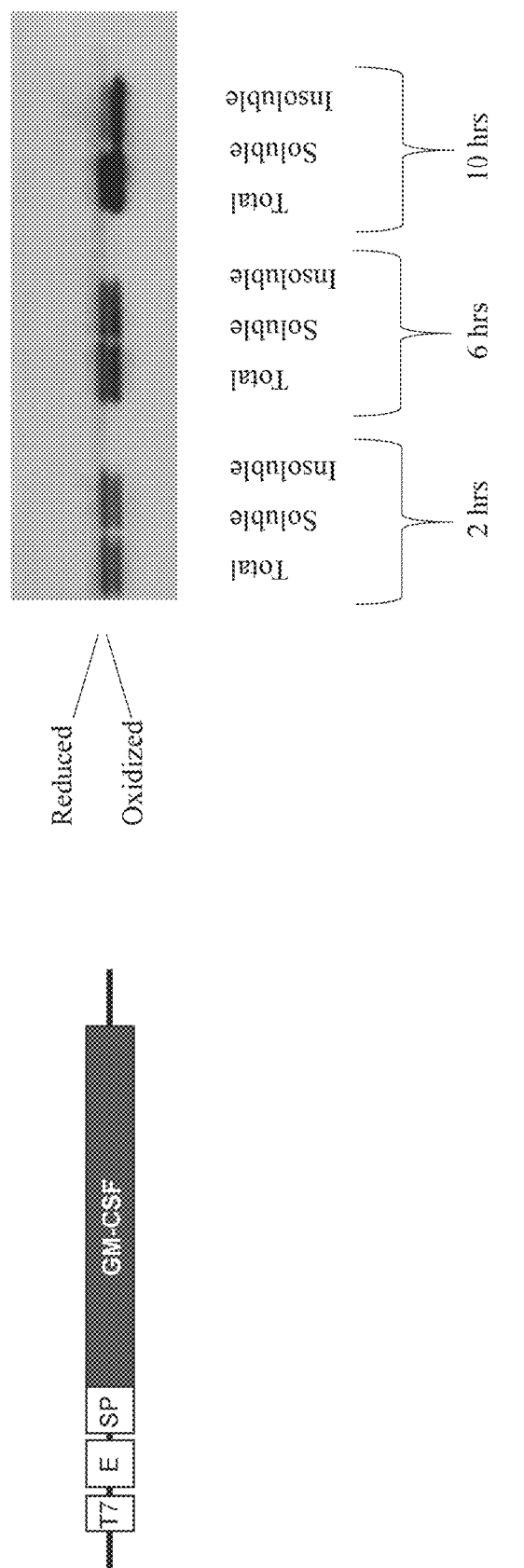
FIG. 11 illustrates expression of human Granulocyte-Macrophage Colony-Stimulating Factor (GM-CSF) from an expression plasmid using a bacterial cell-free protein synthesis system.

Using these conditions, GM-CSF constructs carrying signal peptide sequences upstream of the coding region were expressed in the bacterial CFPS system. Western blot analysis of the GM-CSF product showed that the expressed protein was present almost exclusively in a soluble, oxidized form (FIG. 11). Importantly, the nascent peptide was accurately processed in the lysate generating mature protein having a sequence that was identical to that of the pharmaceutical product (Sargramostim™, a recombinant GM-CSF marketed by Genzyme under the tradename Leukine™). To this end, LC-MS/MS confirmed expected target sequences for GM-CSF produced in the bacterial system (102 of 127 amino acids identified (80.3% coverage)), and confirmed the presence of the correct N-terminal sequence in the protein product as the result of accurate cleavage of the signal peptide sequence from nascent polypeptide.

Using the bacterial CECF protein synthesis system, human GM-CSF was produced at ~2 mg per ml of reaction. Reactions volumes in this system can be scaled up through the use of larger reactors and/or parallelization to allow production of greater amounts and/or higher therapeutic doses of protein biologics, as needed.

Example 11

Figure 12:
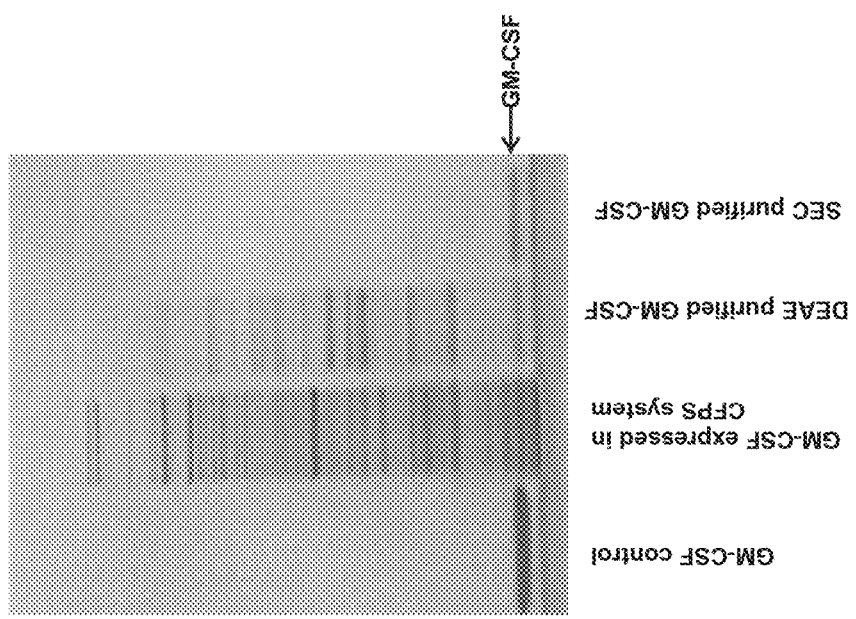
FIG. 12 illustrates purification of GM-CSF expressed in a bacterial cell-free protein synthesis system.

Purification of Human GM-CSF from a Bacterial Cell-Free Protein Synthesis System A modular strategy was developed for continuous flow purification of GM-CSF from bacterial cell-free systems using a combination of Ion EXchange (IEX) and Size Exclusion Chromatography (SEC) steps (FIG. 8B) similar to the method used by Zawada et al., 2011, *Biotechnol. Bioeng.* 108:1570-1578. Briefly, bacterial CFPS samples (1 ml) diluted 1:1 with 10 mM sodium phosphate, pH 6.5, during loading (flow rate of 250 μl/min) onto a 5 cm×1.25 cm (ID) Diethylaminoethyl (DEAE)-Sepharose Fast Flow resin (~6 ml bed volume) (GE Healthcare Bio-Sciences, PA) equilibrated at 10 mM sodium phosphate, pH 6.5. The column was washed and samples were eluted (flow rate of 500 μl/min) with a step gradient using increasing concentrations of NaCl (0 to 1M) in the same sodium phosphate buffer. Western blot analysis showed that almost all of the GM-CSF protein was recovered upon elution with 200 mM NaCl. The entire 200 mM salt fraction was collected, dialyzed and concentrated over a regenerated cellulose 3 kDa molecular weight cut-off membrane (Ultracel, Merk EMD Millipore, MA). Sample fractions containing GM-CSF were pooled, dialyzed, the concentrated samples were loaded on a 6 ml Sephacryl® S200 HR (GE Healthcare Bio-Sciences, PA) size exclusion chromatography column (40:1 length:width, column flow rate of 18-35 μl/min) and developed at a flow rate of 20 μl/min. Total protein in fractionation samples was quantified using a Pierce™ BCA protein assay (Life Technologies Corporation, CA) and GM-CSF purity was assessed in 4-12% SDS-PAGE gels with SimplyBlue SafeStain™ (Life Technologies Corporation, CA) according to the manufacturer's recommendations. The Coomassie blue staining protein profiles of the IEX and SEC column samples are shown in FIG. 12. Purification of GM-CSF produced in the bacterial cell-free system was completed within 8 hours. Protein quantitative assessment indicated that the overall rhGM-CSF recovery was at an estimated 20±3%, thus allowing generation of single dose amounts of protein products from small cell free reaction volumes (1-5 ml).

Example 12

Figure 13:
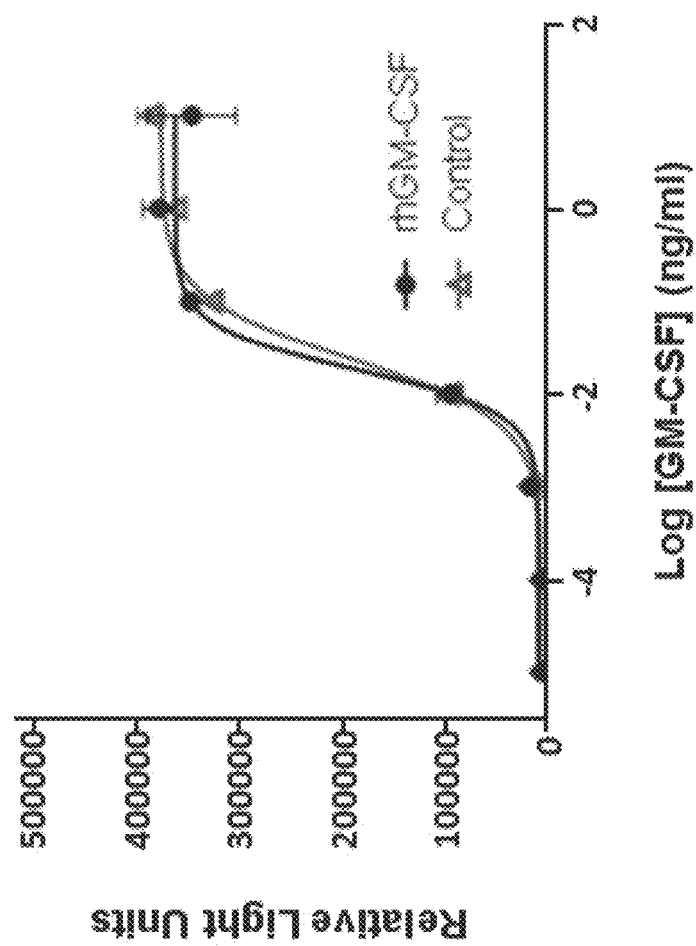
FIG. 13 illustrates activity data of GM-CSF protein produced in a bacterial cell-free protein synthesis system and purified using a non-tag approach.

Activity of Human GM-CSF Purified from a Bacterial Cell-Free Protein Synthesis System GM-CSF was synthesized in a bacterial lysate hosted in a PDMS reactor and purified using the aforementioned fluidic ion exchange and size exclusion chromatography methods. The biological activity of the purified product was evaluated using a standard cell-based assay that monitors the ability of the target protein to induce proliferation of a GM-CSF-depended human cell line, TF-1. The bioactivity assay was performed as described above. End-to-end produced GM-CSF was found to have similar activity to that of a commercially available control protein (FIG. 13). The EC50 was calculated at 0.01823 for the purified GM-CSF expressed in the bacterial cell-free protein synthesis system, whereas the EC50 for the GM-CSF control was 0.02407.

Example 13

Figure 14:
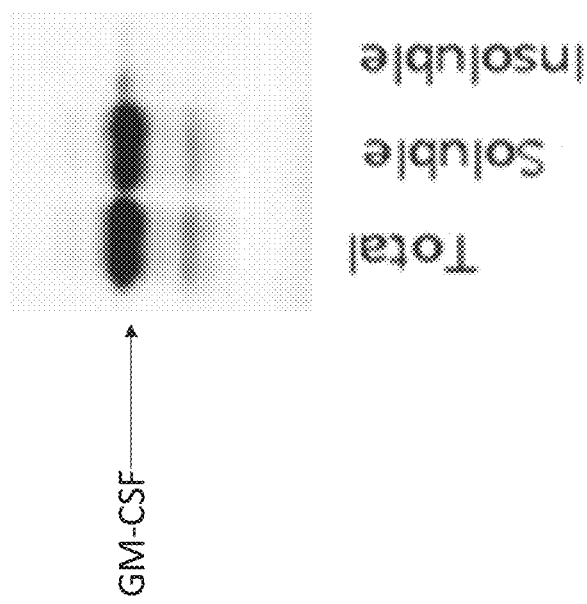
FIG. 14 illustrates expression of GM-CSF carrying an affinity tag in a bacterial cell-free protein synthesis system.
Figure 15:
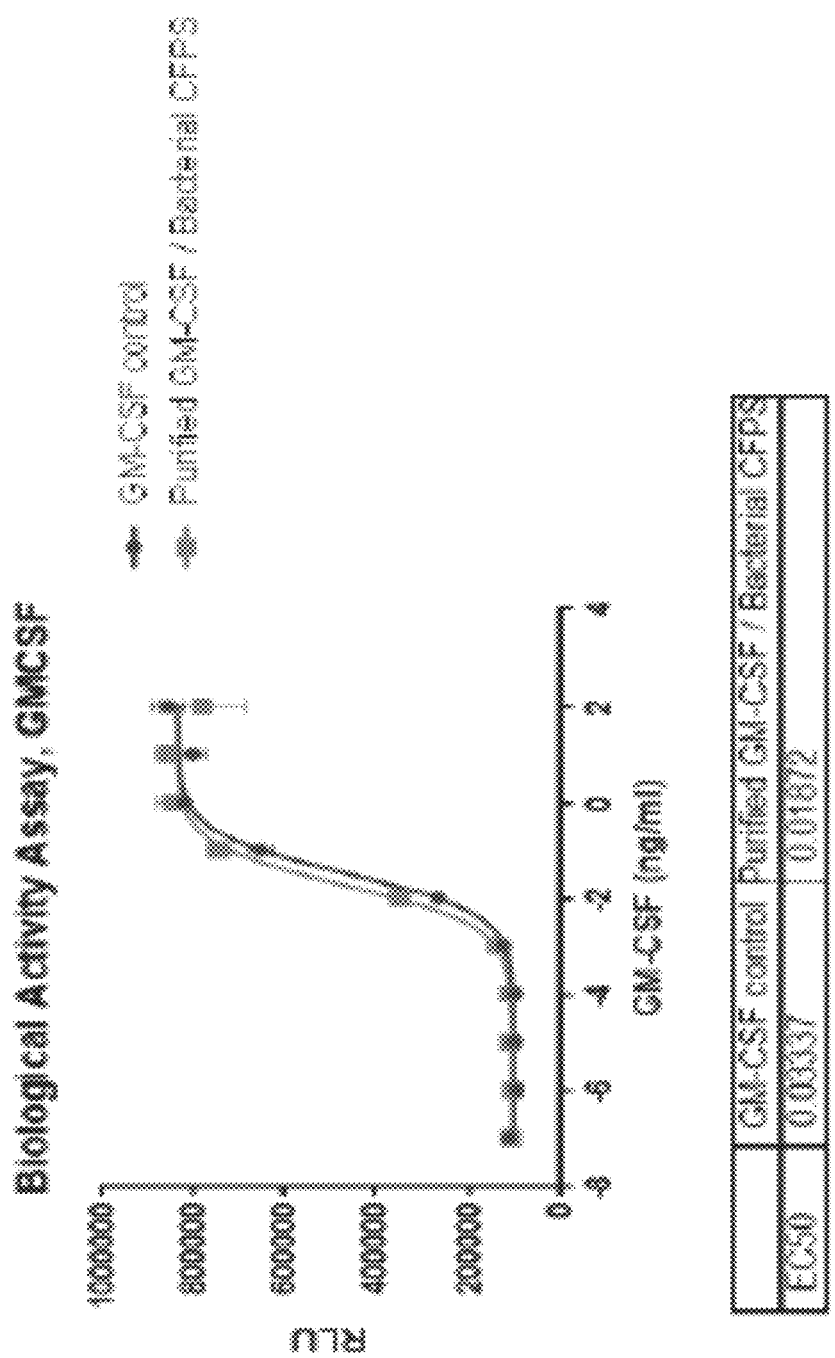
FIG. 15 illustrates activity data of GM-CSF expressed in a bacterial cell-free protein synthesis system and purified using an affinity chromatography approach.

An Affinity FLAG™-Tag Approach for GM-CSF Purification from a Bacterial Cell-Free Protein Synthesis System To demonstrate the system's flexibility, an affinity-based approach for GM-CSF purification from the bacterial platform was developed, similar to the approach described above for EPO purification from the yeast platform. To this end, a construct encoding GM-CSF carrying a FLAG™-tag was generated and subjected to coupled transcription/translation as described above. The synthesized protein was found in the soluble fraction of the reaction (FIG. 14). Protein was purified using the anti-FLAG™ affinity chromatography method and its bioactivity was assessed using the GM-CSF-depended human cell line bioassay as described above. GM-CSF product was found to have similar activity to that of a commercially available control protein (FIG. 15).

Example 14

Figure 16:
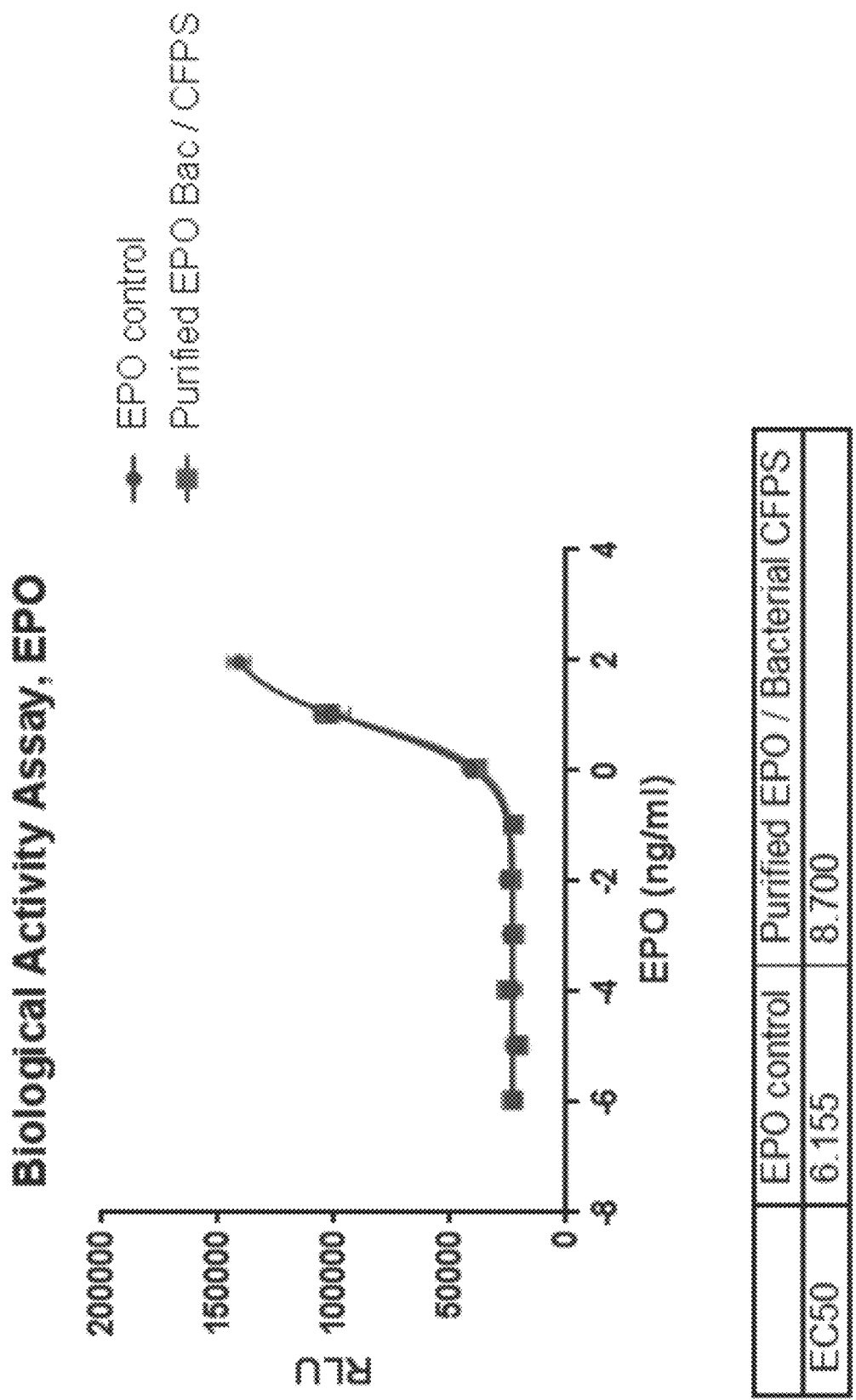
FIG. 16 illustrates activity data of human Erythropoietin expressed in a bacterial cell-free protein synthesis system and purified using an affinity chromatography approach.

Expression, Purification, Posttranslational Modifications, and Activity of Human EPO Produced in a Bacterial Cell-Free Protein Synthesis System To further assess the flexibility of the developed platform, human EPO was expressed in bacterial CFPS system and purified using the aforementioned FLAG™-Tag affinity chromatography approach. LC-MS/MS confirmed human EPO sequence expressed in the bacterial CFPS system ((123 of 166 amino acids were identified (74% coverage)). The biological activity of bacterially expressed and purified EPO was evaluated using a standard cell-based assay that monitors the ability of the target protein to induce proliferation of an EPO-dependent human cell line, TF-1. The results showed that the activity of the protein product was nearly identical to that of a commercial control EPO protein (FIG. 16).

Figure 17:
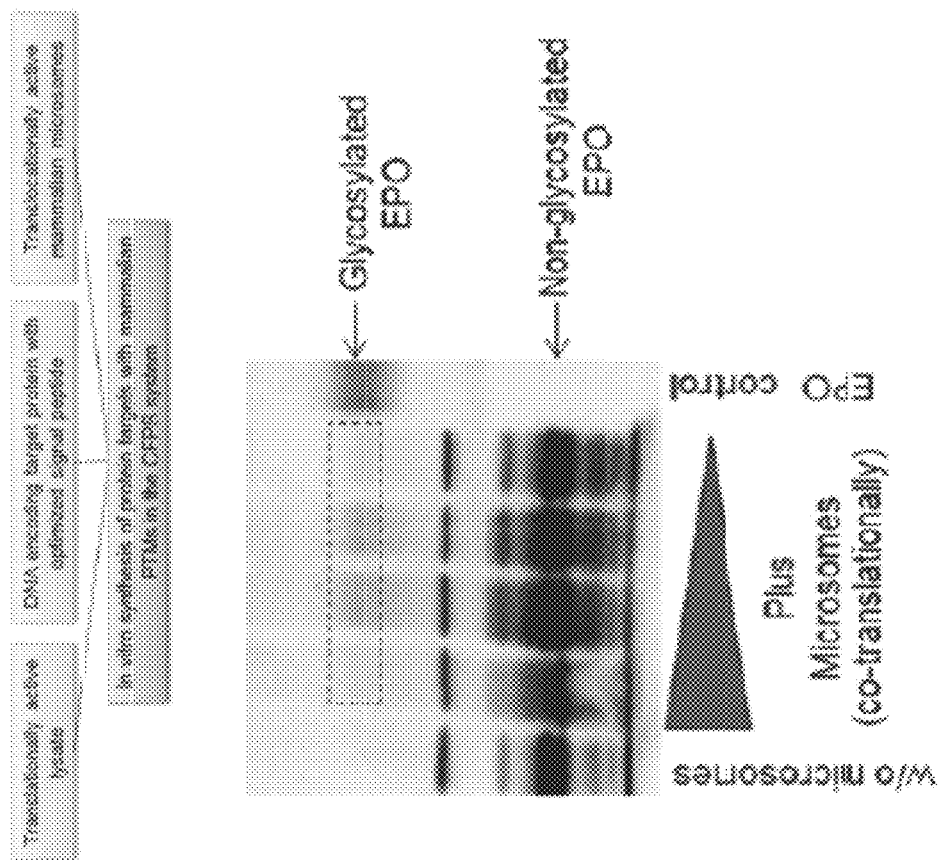
FIG. 17 illustrates in vitro production of human erythropoietin in a bacterial cell-free protein synthesis system combined with the mammalian posttranslational apparatus.

To evaluate the ability of the bacterial CFPS platform to confer human-like glycosylation of target proteins, a heterologous cross-kingdom reconstituted system consisting of the bacterial cell-free translation system and the mammalian translocation machinery was developed. To this end, mammalian-derived SRP, ER and Golgi components were isolated from CHO cells using previously described methods (e.g., Walter and Blobel, 1983, *Methods Enzymol.* 96:84-93) and added to a bacterial CFPS system programmed for EPO expression. FIG. 17 shows the ability of the heterologous reconstituted system to generate EPO protein products having a MW that is similar to that of the glycosylated EPO control protein. Gel samples containing the high MW EPO band were isolated and subjected to Mass Spectrometry analysis; LC-MS analysis confirmed EPO present in the high MW band.

Example 15

Rapid Cell-Free Expression and Purification of Active rhEPO

Enhancement of rhEPO Expression in a Yeast Cell Free System Through Alleviation of Substrate Limitations and mRNA Translation Inhibitory Factors One objective was to enhance product yields and functional activity of rhEPO expressed in a *Saccharomyces cerevisiae*-based CFPS system. This was achieved by a two-fold approach focusing on: a) alleviating the exhaustion of essential substrates (e.g., nucleotide triphosphates and amino acids) that are consumed during protein synthesis and removal of toxic byproducts (e.g., inorganic phosphates) accumulated during protein synthesis (Spirin 2004, *Trends Biotechnol.* 22:538-545; Schoborg et al., 2014, *Biotechnol J.* 9:630-640) and b) eliminating translation initiation inhibitory features, such as canonical and non-canonical initiation codons contained within the coding sequence that cause ribosomal diversion and consequently reduction in the synthesis of the correct, full-length protein product (Matsuda and Mauro, 2010, *PLoS One*, 5, DOI: 10.1371/journal.pone.0015057; Chappell et al., 2006, *Proc. Natl. Acad. Sci. U.S.A.* 103:18077-18082). The former approach involved adaptation of a CECF protein synthesis format that has broadly been utilized for generation of highly productive CFPS systems (Shirokov et al., 2007, *Methods Mol. Biol.* 375:19-55). The latter approach involved the use of synonymous mutations to either remove alternative initiation codons or decrease their utilization contained within the natural EPO signal peptide sequences. Signal peptides are short leader peptides found on the N-terminus of proteins destined for the secretory pathway. Signal peptides are portable, i.e., they can function on different genes, and are cleaved from the nascent polypeptide to generate the mature protein. To this end, EPO constructs carrying recoded signal peptide sequences upstream of the coding region as well as a FLAG™-Tag sequence between the signal peptide and the coding region were generated and subjected to combined transcription/translation in the yeast CECF protein synthesis system (FIG. 6). Using the yeast CECF protein synthesis system, rhEPO was produced at approximately 40 µg per ml of reaction with the majority of the expressed protein being present in the soluble fraction of the CFPS reaction mixture (FIG. 6).

A Modular Fluidic Process for Rapid Purification of Cell-Free Expressed rhEPO

FIG. 6 presents a schematic diagram of the construct used for cell-free expression of rhEPO in the yeast CECF protein synthesis system. The PCR template for rhEPO contains a T7 promoter (T7), translational enhancer (E), signal peptide (SP), and three FLAG™ epitopes, with an enterokinase cleavage site upstream of the mature coding sequence. FIG. 6 also shows a Western blot analysis of rhEPO expression in a yeast cell-free protein synthesis system at 22° C. As can be observed in FIG. 6, the majority of rhEPO expressed in the yeast CFPS system is present in the soluble fraction.

rhEPO expressed in the yeast CFPS system was purified according to the strategy described in FIG. 8A. The first step of the purification process involved separation of the expressed protein from the yeast lysate using anti-FLAG™ affinity chromatography. Typically this step requires overnight incubation of the protein materials with the beads; however, upon optimization of the binding conditions (increasing the ratio of beads to protein) it was possible to reduce this time to 4 hours, during which time almost all available protein was bound to the beads (FIG. 9A).

The next step included elution of the protein off the beads under acidic conditions (pH 3) (FIG. 9A). Treatment of the eluted protein with Enterokinase resulted in cleavage of the FLAG™ epitope from the tagged EPO protein as demonstrated by the reduction in the molecular weight of the protein product (Western blot using anti-EPO antibody, FIG. 9A) and the disappearance of the FLAG™ epitope (Western blot using anti-FLAG™ antibody, FIG. 9B). Enterokinase was then removed via the use of an agarose matrix embedded with soybean trypsin inhibitor that specifically binds to the enzyme. An Enterokinase-specific activity assay showed that this affinity-based enzyme capture step resulted in removal of the Enterokinase from the protein sample (FIG. 9C). The protein product was visualized using a Coomassie blue staining gel (FIG. 9D).

Western blot analysis (anti-EPO) of FLAG™-rhEPO expressed in a yeast cell-free protein synthesis system during the various steps of protein purification. (FIG. 9B). Western blot analysis (anti-FLAG™) of EPO sample before and after Enterokinase treatment for FLAG™-tag removal. (FIG. 9C) The efficiency of the Enterokinase capture and removal step assessed using a fluorogenic substrate-based enzymatic assay; upon enzyme cleavage, this substrate generates a rhodamine fluorophore that is detected at excitation/ emission=490/520 nm. (FIG. 9D) Coomassie blue staining of protein samples before and after FLAG-affinity chromatography.

Mass spectrometry analysis showed that the nascent FLAG™-rhEPO polypeptides synthesized in vitro were accurately processed enzymatically, generating mature rhEPO protein with a sequence that was identical to that of the pharmaceutical product (Epogen, Amgen, Inc., CA). Liquid chromatography-tandem mass spectrometry (LC-MS/MS) using trypsin and Glu-C digests, as well as the overlap between them, confirmed the expected target sequences [86.7% coverage (144 of 166 amino acids) for rhEPO produced in the yeast system] as well as the presence of the correct N-terminal sequence in the rhEPO product as the result of enzymatic cleavage of the FLAG™ tag during the protein purification process (see FIGS. 18-20).

Production of Bioactive rhEPO

A standard EPO-dependent cell viability assay was employed to determine the bioactivity of the purified protein. This assay is based on quantitation of luminescent signal generated in the presence of ATP, which is directly proportional to the number of metabolically active cells present in the well. The results showed that produced EPO has activity that is comparable to that of a commercially available EPO protein (FIG. 10).

Biological activity of rhEPO synthesized in a PDMS-based reactor hosting a yeast CFPS system under continuous exchange format and purified as described in FIG. 8A. Protein biological activity was assessed using a standard human TF-1 cell-based proliferation assay (FIG. 10). Shown are representative results from two biological replicates at multiple rhEPO protein concentrations. Data represent the mean±SD of luminescence relative light units produced in the biological experiments.

Example 16

Rapid Cell Free Expression and Purification of Active rhGM-CSF

Alleviation of mRNA Translation Inhibitory Features and Redox Environment Optimization Increases Expression of Oxidized rhGM-CSF in a Bacterial Cell Free System An assay optimization approach was used to maximize expression of functionally folded human GM-CSF in the bacterial batch CFPS system. Similarly to the aforementioned yeast expression strategy, recoded signal peptides were generated and cloned upstream of the rhGM-CSF coding region to eliminate inhibitory features, such as secondary start sites, and consequently increase the productive ribosomal recruitment to the main mRNA initiation codon in the bacterial cell-free protein synthesis system (FIG. 11). Additionally, cell-free reactions were performed in an oxidizing environment that favors disulfide bond formation (GM-CSF contains two intramolecular disulfide bonds in its native form) and supplemented with specific foldases and chaperone molecules, conditions that have been shown to allow for correct protein folding and synthesis of soluble and active target proteins (Goerke and Swartz, 2008, *Biotechnol. Bioeng.* 99:351-367). This approach included: a) iodoacetamide (IAM) pre-treatment of cell extracts (IAM inactivates reducing activity in lysate by inactivating disulfide-reducing enzymes, such as, for example, thioredoxin reductase), b) adjustment of the redox potential by adding an oxidized glutathione buffer ("GSH/GSSG" containing glutathione (GSH) and glutathione disulfide (GSSG)), and c) addition of an *E. coli* periplasmic disulfide isomerase (DsbC) to facilitate formation of correct disulfide bonds (incorrect disulfide bonds may lead to poor protein folding and aggregation of misfolded proteins) (Goerke and Swartz, 2008, *Biotechnol. Bioeng.* 99:351-367). Addition of nonionic detergents has also been shown to prevent product aggregation and improve solubility of proteins expressed in CSFP systems (Shirokov et al., 2007, *Methods Mol. Biol.* 375:19-55). Accordingly, Brij® 35 was included in the CFPS system. Using these conditions, rhGM-CSF protein was expressed from the aforementioned constructs at approximately 2 mg per ml of reaction and found to be present almost exclusively in a soluble, oxidized form (see FIG. 11). FIG. 11 shows a schematic diagram of the construct used for cell-free expression of rhGM-CSF in the bacterial cell-free protein synthesis system. The plasmid template for rhGM-CSF contains a T7 promoter (T7), translational enhancer (E), and signal peptide (SP) upstream of the mature coding sequence. FIG. 11 also shows a Western blot analysis of cell-free expressed rhGM-CSF in a bacterial lysate. CFPS reaction was performed in the presence of nonionic detergent Brij 35 (0.1%), IAM and DsbC at 30° C.

A Modular Fluidic Process for Rapid Purification of Bacterial Cell-Free Expressed rhGM-CSF rhGM-CSF expressed in the CFPS system was subjected to a protein purification scheme involving ion exchange and size exclusion chromatography (FIG. 8B), similar to the protocol described earlier (Zawada et al., 2011, *Biotechnol. Bioeng.* 108:1570-1578). Bacterial CFPS samples were loaded onto the ion exchange module and subjected to elution with increasing concentrations of NaCl. The 200 mM salt fractions containing rhGM-CSF were pooled, dialyzed, concentrated, and loaded on a size exclusion chromatography module.

The Coomassie blue staining profiles of specific ion exchange and size exclusion samples during the various steps of the purification process are shown in FIG. 12, indicating the isolation of a protein with the expected molecular weight of rhGM-CSF. Commercial human GM-CSF was used as a control. LC-MS/MS analysis also confirmed the production of the expected target sequence [80.3% coverage (102 of 127 amino acids)] for the rhGM-CSF protein expressed in the bacterial system as well as established the presence of the correct N-terminal sequence in the protein product as the result of accurate cleavage of the signal peptide sequence from the nascent polypeptide in the bacterial lysate (see FIGS. 21-23). The correct cleavage of the in vitro expressed rhGM-CSF protein is most likely due to signal peptidase activity present in the bacterial extract used in the CFPS system (Ahn et al., 2007, *Nucleic Acids Res.* 35, DOI: 10.1093/nar/gkl917).

Production of Bioactive rhGM-CSF

The biological activity of the expressed and purified rhGM-CSF product w synthesized in a PDMS-based reactor hosting a bacterial CFPS system under batch format and purified as described in FIG. 8B as evaluated using a standard cell-based assay that monitors the ability of the target protein to induce proliferation of a GM-CSF-dependent human cell line, TF-1. Protein biological activity was assessed using a standard human TF-1 cell-based proliferation assay (FIG. 13). Shown are representative results from two biological replicates at multiple rhGM-CSF protein concentrations. Data represent the mean±SD of luminescence relative light units produced in the biological experiments. Purified GM-CSF was found to have similar activity to that of a commercially available control protein (FIG. 13).

Additional approaches for in vitro protein glycosylation in both the yeast and bacterial CFPS systems are being tested, involving a) incorporation of non-genetically encoded amino acids for site specific glycoform bioconjugation and b) in vitro enzymatic glycosylation. Such approaches may result in the generation of chemically homogeneous glycoproteins in the bacterial or yeast CFPS systems.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

The invention claimed is:

1. A cell-free method for producing an amount of a protein biologic formulation at pharmaceutical dosage levels at a point of need, the method comprising:
loading by a loading module a reaction solution including one or more reaction reagents to a reactor module;
loading by a feeder module a feeding solution to the reactor module, the reactor module having a first chamber and a second chamber divided by a membrane;
receiving at the first chary one or more reaction agents from the loading module;
receiving at the second chamber the feeding solution from the feeder module;
producing by the reactor module a target protein via a process selected from the group consisting of: (i) continuous exchange cell-free (CECF) and (ii) batch protein synthesis;
separating by a chromatography module the target protein from one or more components of the reaction solution; and
formulating by a finishing module the target protein;
wherein the producing, separating and formulating of the target protein are completed within a period of 24 hours.

2. The method of claim 1, wherein: the producing, separating and formulating of the target protein are completed within a period of 12 hours.

3. The method of claim 1, wherein: the producing, separating and formulating of the target protein are completed within a period of 10 hours.

4. The method of claim 1, wherein the target protein is produced in an amount between about 40 µg/ml and about 8 mg/ml protein.

5. The method of claim 1, further comprising:
facilitating by a control system purification of different proteins on the same platform via switching among various chromatography matrices.

6. The method of claim 1, further comprising:
removing via one or more sampling ports sample aliquots from the reaction chamber for assessment of protein synthesis and formulation processes.

7. The method of claim 1, further comprising:
directing fluidics between one or more of the loader, feeder, reactor, chromatography and finishing modules and facilitating addition and removal of a solution, including the reaction solution and the feeding solution.

8. The method of claim 1, wherein:

formulating includes size exclusion using a chromatography matrix.

9. The method of claim 1, wherein:

separating the target protein employs at least one of (a) tag based affinity chromatography, (b) protease affinity chromatography, and (c) size exclusion chromatography steps, or a combination thereof.

10. The method of claim 1, wherein:

separating the target protein employs at least one of (a) ion-exchange chromatography, (b) protein concentration, and (c) size exclusion chromatography steps, or a combination thereof.

11. A cell-free method for producing an amount of at least one protein biologic formulation at pharmaceutical dosage levels at a point of need, the method comprising:

loading by a loading module a reaction solution including one or more reaction reagents to a reactor module;

loading by a feeder module a feeding solution to the reactor module, the reactor module having a first chamber and a second chamber divided by a membrane;

receiving at the first chamber the one or more reaction agents from the loading module;

receiving at the second chamber the feeding solution from the feeder module;

producing by the reactor module a target protein via a process selected from the group consisting of: (i) continuous exchange cell-free (CECF) and (ii) batch protein synthesis;

monitoring the produced target protein by one or more analytical modules to asses target protein purity level;

directing the produced target protein to one of multiple separation modules in accordance with target protein requirements;

separating the target protein from one or more components of the reaction solution; and formulating by a finishing module the target protein;

wherein the producing, monitoring, directing, separating and formulating of the target protein are completed within a period of 24 hours.

12. The method of claim 11, wherein: the producing, separating and formulating of the target protein are completed within a period of 12 hours.

13. The method of claim 11, wherein: the producing, separating and formulating of the target protein are completed within a period of 10 hours.

14. The method of claim 11, wherein monitoring the produced target protein by one or more analytical modules includes removing via one or more sampling ports sample aliquots from the reaction chamber.

15. The method of claim 11, wherein the target protein is produced in an amount between about 40 µg/ml and about 8 mg/ml protein.

16. The method of claim 11, further comprising:

facilitating by a control system purification of different proteins on the same platform via switching among various chromatography matrices.

17. The method of claim 11, further comprising:

directing fluidics between one or more of the loader, feeder, reactor, chromatography and finishing modules and facilitating addition and removal of a solution, including the reaction solution and the feeding solution.

18. The method of claim 11, wherein:

formulating includes size exclusion using a chromatography matrix.

19. The method of claim 11, wherein:

separating the target protein employs at least one of (a) tag based affinity chromatography, (b) protease affinity chromatography, and (c) size exclusion chromatography steps, or a combination thereof.

20. The method of claim 11, wherein:

separating the target protein employs at least one of (a) ion-exchange chromatography, (b) protein concentration, and (c) size exclusion chromatography steps, or a combination thereof.

* * * * *